US012350615B2

(12) United States Patent
Turbett et al.

(10) Patent No.: US 12,350,615 B2
(45) Date of Patent: *Jul. 8, 2025

(54) STERILIZING METHOD AND APPARATUS

(71) Applicant: Turbett Surgical, Inc., Rochester, NY (US)

(72) Inventors: Robert E. Turbett, Penfield, NY (US); Brian E. McGrath, Clarence, NY (US); Richard D. Richmond, Canandaigua, NY (US)

(73) Assignee: Turbett Surgical, Inc., Henrietta, NY (US)

( * ) Notice: Subject to any disclaimer, the term of this patent is extended or adjusted under 35 U.S.C. 154(b) by 585 days.

This patent is subject to a terminal disclaimer.

(21) Appl. No.: 17/062,976

(22) Filed: Oct. 5, 2020

(65) Prior Publication Data

US 2021/0023491 A1 Jan. 28, 2021

Related U.S. Application Data

(63) Continuation of application No. 16/550,942, filed on Aug. 26, 2019, now Pat. No. 10,792,602, which is a (Continued)

(51) Int. Cl.
*A61L 2/07* (2006.01)
*A61L 2/26* (2006.01)
(Continued)

(52) U.S. Cl.
CPC .......... *B01D 46/0005* (2013.01); *A61L 2/26* (2013.01); *B01D 46/0002* (2013.01); (Continued)

(58) Field of Classification Search
CPC ..... A61L 2/07; A61L 2/26; A61L 2/06; A61L 2/20; A61M 1/1656; A61M 1/288; F24F 13/28; F24F 8/50
(Continued)

(56) References Cited

U.S. PATENT DOCUMENTS 3,691,140 A 9/1972 Silver
4,549,887 A 10/1985 Joannou
(Continued)

FOREIGN PATENT DOCUMENTS

CN 201064700 Y 5/2008
JP 2009285009 A 12/2009
(Continued)

OTHER PUBLICATIONS

European Patent Office, Office Action in corresponding EP Application No. 16774196.6, dated Oct. 7, 2020.
(Continued)

*Primary Examiner* — Monzer R Chorbaji
(74) *Attorney, Agent, or Firm* — Jodi A. Reynolds, Esq.; Harter Secrest & Emery LLP

(57) ABSTRACT

A sterilization container for retaining surgical instruments in a sterilizer comprising a plurality of walls defining an interior volume sized to receive at least one instrument tray, least one of the walls defining a venting pass through area, and a filter occluding the venting passage area, wherein a ratio of the venting pass through area to the interior volume is at least 1 square inch:125 cubic inches.

17 Claims, 35 Drawing Sheets

Related U.S. Application Data continuation of application No. 15/946,442, filed on Apr. 5, 2018, now Pat. No. 10,391,435, which is a continuation-in-part of application No. 15/461,895, filed on Mar. 17, 2017, now Pat. No. 10,226,728, which is a continuation of application No. 14/584,751, filed on Dec. 29, 2014, now Pat. No. 9,616,368, which is a continuation-in-part of application No. 14/167,691, filed on Jan. 29, 2014, now Pat. No. 10,245,335, application No. 17/062,976 is a continuation of application No. 16/229,995, filed on Dec. 21, 2018, now Pat. No. 10,987,438, which is a continuation of application No. 15/662,873, filed on Jul. 28, 2017, now Pat. No. 10,188,762, which is a continuation of application No. 14/675,048, filed on Mar. 31, 2015, now Pat. No. 9,724,438, which is a continuation-in-part of application No. 14/167,681, filed on Jan. 29, 2014, now Pat. No. 9,244,078, and a continuation-in-part of application No. 14/584,751, filed on Dec. 29, 2014, now Pat. No. 9,616,368, which is a continuation-in-part of application No. 14/167,691, filed on Jan. 29, 2014, now Pat. No. 10,245,335.

(60) Provisional application No. 62/482,170, filed on Apr. 5, 2017, provisional application No. 62/482,683, filed on Apr. 6, 2017, provisional application No. 62/483,008, filed on Apr. 7, 2017.

(51) Int. Cl.
  *B01D 25/02* (2006.01)
  *B01D 29/54* (2006.01)
  *B01D 46/00* (2022.01)
  *B01D 46/62* (2022.01)
  *B01D 46/10* (2006.01)
  *B01D 46/64* (2022.01)

(52) U.S. Cl.
  CPC ............ *B01D 46/62* (2022.01); *A61L 2/07* (2013.01); *A61L 2202/121* (2013.01); *A61L 2202/15* (2013.01); *A61L 2202/182* (2013.01); *A61L 2202/23* (2013.01); *A61L 2202/24* (2013.01); *B01D 46/10* (2013.01); *B01D 46/64* (2022.01); *Y10T 29/49826* (2015.01)

(58) Field of Classification Search
  USPC .............. 96/11; 119/417; 312/229; 422/28
  See application file for complete search history.

(56) References Cited

U.S. PATENT DOCUMENTS

| | | |
|---|---|---|
| 4,915,918 A | 4/1990 | Nichols |
| 5,320,733 A | 6/1994 | Boehm |
| 5,464,461 A | 11/1995 | Whitson et al. |
| 5,732,510 A | 3/1998 | Sutton et al. |
| 8,241,381 B2 | 8/2012 | Braunecker et al. |
| 8,454,901 B1* | 6/2013 | Snyder, III .............. A61L 2/26 422/26 |
| 9,616,368 B2 | 4/2017 | Turbett et al. |
| 9,724,438 B2* | 8/2017 | Turbett .................. A61L 2/07 |
| 10,188,762 B2* | 1/2019 | Turbett .................. A61L 2/07 |
| 10,226,728 B2 | 3/2019 | Turbett et al. |
| 10,245,335 B2* | 4/2019 | Turbett .................. A61L 2/07 |
| 10,391,435 B2 | 8/2019 | Turbett et al. |
| 10,675,576 B2* | 6/2020 | Turbett ............. B01D 46/0002 |
| 10,702,616 B2 | 7/2020 | Turbett |
| 10,792,602 B2 | 10/2020 | Turbett et al. |
| 10,881,997 B2 | 1/2021 | Turbett |
| 10,987,438 B2 | 4/2021 | Turbett |
| 11,305,222 B2 | 4/2022 | Turbett |
| 11,819,791 B2 | 11/2023 | Turbett et al. |
| 11,896,924 B2 | 2/2024 | Turbett et al. |
| 2004/0256269 A1 | 12/2004 | Gleichauf et al. |
| 2007/0266681 A1 | 11/2007 | Grey et al. |
| 2012/0241391 A1 | 9/2012 | Carlson et al. |
| 2012/0291406 A1* | 11/2012 | Crabtree ............... B01D 46/58 55/482 |
| 2023/0045343 A1 | 2/2023 | Turbett et al. |
| 2023/0173421 A1 | 6/2023 | Turbett et al. |
| 2024/0033668 A1 | 2/2024 | Turbett et al. |

FOREIGN PATENT DOCUMENTS

| | | |
|---|---|---|
| WO | 2004012779 A1 | 2/2004 |
| WO | 2010091448 A1 | 8/2010 |
| WO | 2011074404 A1 | 6/2011 |
| WO | 2015116356 A1 | 8/2015 |
| WO | 2016161112 A1 | 10/2016 |

OTHER PUBLICATIONS

European Patent Office, Office Action in corresponding EP Application No. 15743752.6, dated Jun. 14, 2021.

Indian Patent Office, First Examination Report in corresponding IN Application No. 201617028262, dated Oct. 12, 2020.

Intellectual Property India, Examination Report under Sections 12 & 13 in corresponding Indian Patent Application No. 201918049471, mailed Feb. 16, 2022 (5 pgs).

Indian Patent Office, First Examination Report in corresponding IN Application No. 202118061824, dated Jun. 16, 2022.

European Patent Office, Extended European Search Report in Corresponding EP Application No. 23178775.5, dated Mar. 14, 2024.

* cited by examiner

STERILIZING METHOD AND APPARATUS

CROSS-REFERENCE TO RELATED APPLICATIONS

This application is a continuation of U.S. patent application Ser. No. 16/550,942 filed Aug. 26, 2019, which is a continuation of U.S. patent application Ser. No. 15/946,442 filed Apr. 5, 2018, now U.S. Pat. No. 10,391,435, which claims the benefit of U.S. Provisional Applications No. 62/482,170 filed Apr. 5, 2017, 62/482,683 filed Apr. 6, 2017, and 62/483,008 filed Apr. 7, 2019, and which is a continuation-in-part of U.S. patent application Ser. No. 15/461,895 filed Mar. 17, 2017, now U.S. Pat. No. 10,226,728, which is a continuation of U.S. patent application Ser. No. 14/584,751 filed Dec. 29, 2014, now U.S. Pat. No. 9,616,368, which is a continuation-in-part of U.S. patent application Ser. No. 14/167,691 filed Jan. 29, 2014, now U.S. Pat. No. 10,245,335, the entire disclosure of each is hereby expressly incorporated by reference.

This application is also a continuation of U.S. patent application Ser. No. 16/229,995 filed on Dec. 21, 2018, which is a continuation of U.S. patent application Ser. No. 15/662,873 filed on Jul. 28, 2017, now U.S. Pat. No. 10,188,762, which is a continuation of U.S. patent application Ser. No. 14/675,048 filed on Mar. 31, 2015, now U.S. Pat. No. 9,724,438, which is a continuation-in-part of U.S. patent application Ser. No. 14/167,691 filed on Jan. 29, 2014, now U.S. Pat. No. 10,245,335 and U.S. patent application Ser. No. 14/584,751 filed on Dec. 29, 2014, now U.S. Pat. No. 9,616,368, which is a continuation-in-part of U.S. application Ser. No. 14/167,691 filed on Jan. 29, 2014, now U.S. Pat. No. 10,245,335, the entire disclosure of each is hereby expressly incorporated by reference.

BACKGROUND OF THE INVENTION

Field of the Invention

Exemplary embodiments of the present disclosure relate to a method and apparatus for sterilization and more particularly to a method and apparatus for sterilization of instruments, wherein a ratio of venting pass through area to volume of the sterilization container is at least a given value, and wherein the given value in select configurations can provide a drying time of less than 30 minutes and in select configurations less than 15 minutes.

Description of Related Art

Sterilization is a term referring to any process that eliminates (removes) or kills microbial life, including transmissible agents (such as fungi, bacteria, viruses, or spore forms) present on a surface, or contained in a fluid, or in medication, or in a compound such as biological culture media. Sterilization can be achieved by applying heat, chemicals, irradiation, high pressure, and filtration or combinations thereof.

In general, surgical instruments and medications that enter an already aseptic part of the body (such as the bloodstream, or penetrating the skin) must be sterilized to a high sterility assurance level. Examples of such instruments include scalpels, hypodermic needles and implantable medical devices (IMD), such as artificial pacemakers.

A widely used method for heat sterilization is the autoclave, sometimes referred to as a sterilizer. Autoclaves commonly use steam heated to 121-134° C. To achieve a degree of sterility, a holding time of at least 15 minutes at 121° C. at 100 kPA, or 3 minutes at 134° C. at 100 kPa is required. Additional sterilizing time is usually required for liquids and instruments packed in layers of cloth, as they may take longer to reach the required temperature.

One method of sterilization involves passing steam through a container. For effective sterilization, steam needs to penetrate the container load uniformly. Accordingly, the container must not be overcrowded, and the lids of bottles and containers must be left ajar. During the initial heating of the container, residual air must be removed. Indicators should be placed in the most difficult places for the steam to reach to ensure that steam actually penetrates there.

A filter is typically placed over the vent to keep particles or extraneous materials from entering the container before, during or after the sterilizing process. Once the sterilizing process is completed, the filter needs to be removed and inspected by medical professionals to verify the integrity of the sterilizing process was maintained. If it is discovered during inspection that the filter did not remain intact, the sterilizing process has to be repeated with a new filter. Further, if moisture is present in the container, the load would be rejected by the user and sent for reprocessing. Thus, a sufficient drying time, wherein there is no visible moisture on the sterilized medical instruments, is needed before the sterilization processing is complete.

The amount of drying time needed to achieve a dry load can be significant. Dry time can add several minutes to the total processing time in order to achieve a load where the instruments are dry. Further, heavier loads, for example, those with a large metal mass, can cause moisture to be maintained inside the container after the sterilization cycle is complete. Thus, weight limits may be required to avoid wet, unsterilized loads after processing. In existing devices, a sterilization cycle may run for 4 minutes at 270° F., followed by at least a 30 minute dry cycle. These containers have relatively small vent area to volume ratios, wherein an area of the vent is small compared to the internal volume of the container. For example, in the S.C.O.R.E.S. container labelled by PMBS, LLC of Stockton N.J., the ratio of the area of the vent to volume is approximately 0.004-0.006 in$^2$ per in$^3$. These vent area to volume ratios limit circulation through the container, contribute to the longer dry times required for achieving a dry load, and significantly limit the weight of the load that can be placed into the container.

What is needed, then, is a sterilization container for retaining surgical instruments in a sterilizer that has improved circulation and evaporation and shorter drying times.

BRIEF SUMMARY OF THE INVENTION

In view of the foregoing, a sterilization container for retaining a surgical instrument in a sterilizer is provided.

A first exemplary embodiment provides a sterilization container for retaining surgical instruments in a sterilizer. The sterilization container comprises an enclosing wall and a door defining an interior volume sized to receive at least one instrument tray, at least one of the enclosing wall and the door defining a venting pass through area, and a filter occluding the venting pass through area, wherein a ratio of the venting pass through area to the interior volume is at least 0.008 inch$^2$ per inch$^3$, and in select configurations at least 0.016 inch$^2$ per inch$^3$, and in further configurations greater than 0.02 inch$^2$ per inch$^3$. In further configurations, the ratio of the venting pass through area to the interior volume is between least 0.008 inch$^2$ per inch$^3$ and 0.2 inch$^2$ per inch$^3$ and in select configurations between 0.016 inch$^2$ per inch$^3$, and 0.2 inch$^2$ per inch$^3$.

The enclosing wall of the sterilization container can be any of a variety of configurations, such as but not limited to defining polygonal containers, containers with curvilinear walls or combinations thereof. For purposes of description, the sterilization container has been set for in terms of walls forming the enclosing wall. Thus, in a further configuration, the sterilization container comprises an enclosing wall having a plurality of walls and a door defining an interior volume sized to receive at least one instrument tray, at least one of the walls and the door defining a venting pass through area, and a filter occluding the venting passage area, wherein a ratio of the venting pass through area to the interior volume is at least 0.008 inch$^2$ per inch$^3$, and in select configurations at least 0.16 inch$^2$ per inch$^3$, and in further configurations greater than 0.2 inch$^2$ per inch$^3$.

Further, the configurations are set forth in terms of a sterilization container, which encompasses a sterilization cabinet.

Another exemplary embodiment provides a method of drying contents in a sterilization container, the method comprising sterilizing contents in a sterilization container having an enclosing wall, such as a plurality of walls, and a door defining an interior volume sized to receive at least one instrument tray retaining the contents, venting the sterilization container through a venting pass through area having a filter occluding the venting passage area, wherein a ratio of the venting pass through area to the interior volume is at least 0.008 inch$^2$ per inch$^3$, and obtaining a drying of the contents in the sterilizing cabinet in less than 30 minutes and in select configurations less than 15 minutes.

A further exemplary embodiment provides a sterilization container for retaining surgical instruments in a sterilizer, the sterilization container comprising an enclosing wall, such as a plurality of walls and a door defining an interior volume sized to receive at least one instrument tray, at least one of the enclosing wall and the door defining a venting pass through area, and a filter occluding the venting passage area, the sterilization container having a ratio of the venting pass through area to the interior volume sufficient to provide a drying time of less than 30 minutes and in select configurations less than 15 minutes.

Yet another exemplary embodiment provides a sterilization container for sterilizing instruments in a sterilizer using a sterilizing agent, the sterilization container comprising an opening defined by a perimeter of an enclosing wall, the enclosing wall defining an interior volume sized to receive a plurality of instrument trays, a door moveable between an open position and a closed position, wherein the interior volume is accessible through the opening when the door is in the open position, and a filter cartridge having a gasket surrounding a first filter comprising a porous material wherein the filter cartridge is removably secured to the door when the door is in the open position, and wherein the gasket is positioned between the door and the enclosing wall to form a sealed interface between at least one of the door and the enclosing wall when the door is in the closed position.

Another exemplary embodiment provides a sterilization container for sterilizing instruments in a sterilizer using a sterilizing agent, the sterilization container comprising an enclosing wall and a door defining a total surface area and an interior volume sized to receive a plurality of instrument trays, at least one of the enclosing wall and the door defining a venting pass through area, wherein the door is moveable between an open position and a closed position, and wherein the interior volume is accessible when the door is in the open position, and a filter cartridge having a gasket surrounding a first filter, wherein the filter cartridge provides sufficient structural integrity to form a sealing interface with at least one of a confronting surface of the enclosing wall and the door, wherein the first filter occludes the venting pass through area, and wherein the venting pass through area is at least 5.7% of the total surface area.

A further exemplary embodiment provides a method of sterilizing items in a sterilization container, the method comprising placing items to be sterilized into an interior volume of a sterilization container having at least one door, the interior volume defined by an enclosing wall, the enclosing wall and door defining a total surface area of the sterilization container, and securing a filter cartridge having a gasket surrounding a first filter to the door, wherein the filter cartridge is sized to position the gasket between confronting surfaces of the door and the enclosing wall to engage at least one of the door and the enclosing wall when the door is in a closed position.

The method of sterilizing items in a sterilization container may further comprise the steps of securing the door in the closed position to compress the gasket and form a sealed interface between at least one of the door and the enclosing wall, and sterilizing items in the sterilization container in a sterilizer wherein the sterilization container is vented through a venting pass through area having the first filter occluding the venting pass through area, wherein the venting pass through area is at least 5.7% of the total surface area.

Further, the method of sterilizing items in a sterilization container may further comprise the step of drying the items in the sterilization container in less than 30 minutes, moving the door into an open position, wherein the filter cartridge remains secured to the door, releasing the filter cartridge from the door, and disposing of the filter cartridge.

BRIEF DESCRIPTION OF THE SEVERAL VIEWS OF THE DRAWING(S)

DETAILED DESCRIPTION OF THE INVENTION

Figure 1A:
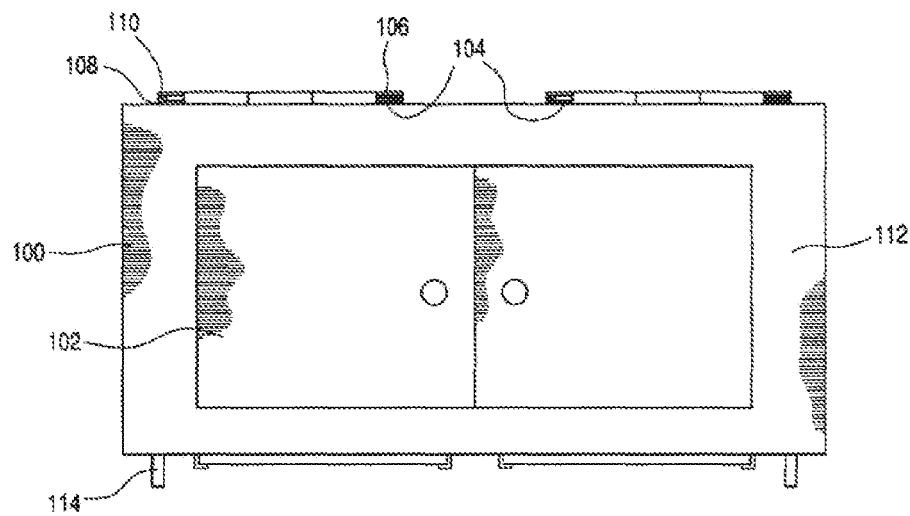
FIG. 1a is a front view of a configuration of a sterilization container such as a sterilization cabinet suitable for use in practicing exemplary embodiments of this disclosure.

In the medical field, it is of the utmost importance that medical instruments are sterilized prior to any medical procedure. This drastically helps prevent the spread of infectious materials. In the marketplace, there are a wide variety of devices that provide for sterilization of medical instruments through the use of a sterilizing agent, such as steam. Instrument trays can be wrapped in a cloth or paper that acts as a filter, allowing the tray to be sterilized, then delivered to the operating room. Alternatively, a rigid container can contain the instrument tray. The device (e.g., a rigid container, sterilization container or cabinet) contains at least one vent for venting the steam used to sterilize the contents of the device. A disposable filter usually covers these vents. The filters have two major purposes. First, the filters prevent extraneous materials from entering the sterilizing device during and after the sterilization cycle. Second, the filters allow sterilizing steam to enter and exit the sterilizing device (sterilization container). Thus, the sterilization container can retain the sterilized medical instruments within the container and protected from the environment by the filters sealing the vents. The filter can be made of any type of porous paper or cellulose type material. In other embodiments, the filter is made of polymeric substances, such as polypropylene or a combination such as plasticized paper as known in the art. The filter is required to be both porous and dense enough to allow the passage of a sterilizing agent, such as steam, through its membrane, but also resilient enough to not rip or tear during a sterilizing cycle or during insertion/clamping into operable position. Although the present description is set forth in terms of a paper-like filter, the filter can be a tortuous path or even a valve that acts as a check valve permitting the venting of the sterilization container without permitting passage of extraneous materials into the sterilization container.

Referring to FIGS. 1a-3b, the sterilization container 100, alternatively referred to as the sterilization cabinet is shown. For purposes of the present description, the sterilization container is set forth as a sterilization cabinet. However, it is understood, the disclosure is not limited to the sterilization cabinet and can be any sterilization container. And further, it should be noted that embodiments of the present invention are not limited to the particular configuration of sterilizing cabinet 100.

The term sterilization cabinet 100 encompasses any device capable of retaining the medical instruments subjected to the sterilization procedure, wherein the cabinet 100 can receive and retain at least one tray, with the tray retaining at least one medical instrument. The sterilization cabinet 100 can retain the medical instruments in the sterilized condition after the sterilization process. The term sterilization container also includes sterilizing cabinets for sterilizing medical instruments, surgical devices and the like. The term sterilizer includes, but is not limited to, a housing or device defining an interior retaining the sterilization container and in which a controlled environment is create to impart a desired sterilization. Sterilizers include autoclaves; hot air ovens; ethylene oxide; low temperature steam, steam, high pressure steam and formaldehyde; sporicidal chemicals; irradiation; chlorine dioxide (CD) gas sterilization; hydrogen peroxide; vaporized hydrogen peroxide; hydrogen peroxide plasma; electron beam and gas plasma devices.

The sterilization cabinet 100 includes an enclosing wall which defines an interior volume, wherein the enclosing wall can include a plurality of sidewalls, a top wall and a bottom wall. The walls can be planar or curvilinear and can be oriented to define a rectilinear volume, cubic volume or round or curved volume. For purposes of the present disclosure, the enclosing wall is set forth as the plurality of sidewalls, the top wall and the bottom wall, along with a door. It is understood the enclosing wall can include or cooperate with a door to at least partially define the interior volume. In one configuration the sterilization cabinet 100 includes the enclosing wall having the plurality of sidewalls, the top wall and the bottom wall, along with a door or doors 102, vents 104, and in certain configurations filter holder 106, primary filter 108, secondary filter 110, sterilization cabinet frame 112 and legs 114. Door or doors 102 are able to open and close for access to the interior of sterilizing cabinet 100. Door or doors 102 are physically connected to sterilization cabinet frame 112. Door or doors 102 can be attached through the use of a hinge or hinges which allows the doors to swing open. Alternatively, door or doors 102 can be removable from sterilization cabinet 100 through the use of clamps (not shown in FIG. 1). It should be appreciated that exemplary embodiments of door or doors 102 include any mechanism that allows for door or doors 102 to move from an open position to a closed position to provide access to the interior of sterilization cabinet 100. The door can effectively form a wall of the sterilization cabinet, as seen in the Figures.

Sterilization cabinet 100 in one embodiment provides for four vents 104. However, it should be appreciated that exemplary embodiments of sterilization cabinet 100 are not limited to four vents. The sterilization cabinet 100 may include a fewer number or a greater number of vents 104. The vents 104 can define a venting pass through area 140 of the sterilization cabinet 100. It should be appreciated that vents 104 can provide numerous small openings for the passage of sterilizing steam or heat. The small openings in vents 104 can be holes or slits. Alternatively, vents 104 can be fenestrated. By "venting pass through area" it is meant to refer to the total available area for the ingress and egress of a gas to or from the interior volume of the sterilizing cabinet 100. Exemplary embodiments of sterilization cabinet 100 can include one or more vents so long as the venting pass through area to volume ratio is equal to or greater than 0.008 inch$^2$ per inch$^3$, or 1 inch$^2$: 125 inch$^3$, and in select configurations between 0.02-0.2 inch$^2$ per inch$^3$, or between 1 inch$^2$:50 inch$^3$ and 1 inch$^2$:5 inch$^3$, and in further configurations between 0.16-0.2 inch$^2$ per inch$^3$, or 4 inch$^2$:25 inch$^3$ and 1 inch$^2$:5 inch$^3$.

The term "dry time" or "drying time" means the time required to provide no visible moisture in the sterilization container or on the sterilized medical instrument (or tray or wrapping, if used), as set forth in the governing regulations. For example, as set forth in AAMI ST79 Comprehensive guide to steam sterilization and sterility assurance in health care facilities (AAMI/CDV-2 ST79), visible moisture left in (interior) or on (exterior) a package or tray within the sterilization container after sterilization and the proper cooling (drying) period should be considered a wet pack. Further, if moisture is present on or in two or more packages the load should be considered a wet load. The moisture may be in the form of visible dampness, droplets, or puddles of water on or within a pack (or instrument or tray). If wet packs are observed in the processing area they should not be released. If wet packs are observed in the user area (e.g., in the OR) they should not be used.

Figure 1B:
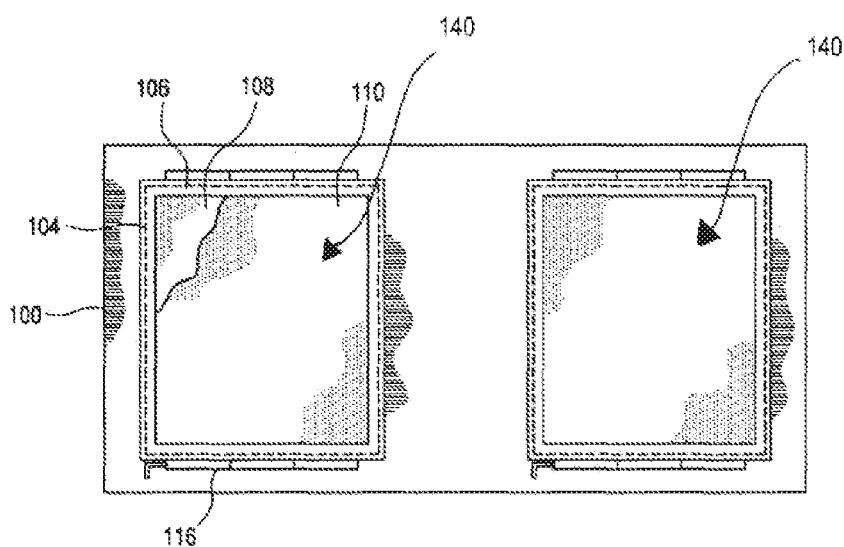
FIG. 1b is a top view of a configuration of a sterilization container such as a sterilization cabinet suitable for use in practicing exemplary embodiments of this disclosure.

By "venting pass through area to volume ratio," it is meant the ratio of the total venting pass through area 140 of a sterilizing cabinet 100 to the interior volume of the sterilization cabinet 100 ratio. Thus, for example, a sterilizing cabinet 100 as shown in FIGS. 1a and 1b, with four vents 104, two vents 104 on the top of the sterilizing cabinet 100 and two vents 104 on the bottom of the sterilizing cabinet 100, each venting area having a venting area of approximately 11.4 inches ($L_2$)×13 inches ($W_2$), will have a total venting area of approximately 592 square inches. The volume of the sterilization cabinet 100, wherein the length is approximately 34 inches ($L_1$), the width is approximately 17 inches ($W_1$), and the height is approximately 17 inches (Hi), is approximately 9826 inches $^3$. Thus, sterilization cabinet 100 as shown in FIGS. 1a-2b would have a venting pass through area to volume ratio of approximately 0.06 inch$^2$ per inch$^3$. In other exemplary embodiments of the sterilization cabinet 100, the venting pass through area to volume ratio is between approximately 0.02-0.2 inch$^2$ per inch$^3$, or 1 square inch:50 cubic inches and 1 square inch:5 cubic inches, and in some configurations between 0.16-0.2 inch$^2$ per inch$^3$, or 4 square inches:25 cubic inches and 1 square inch:5 cubic inches. The high venting pass through area to volume ratio increases circulation and evaporation and reduces the drying time required after the sterilization cycle. It should be appreciated that exemplary embodiments of the sterilizing cabinet can be other dimensions, shapes and sizes that provide similar vent to volume ratios. For example, the upper limit of the venting pass through area to volume ratio is 6 inch$^2$ to 1 inch$^3$. However, from manufacturing considerations and structural requirements, the upper range of the venting pass through area to volume ratio is typically between 2.5 inch$^2$ and 6 inch$^2$ to 1 inch$^3$.

The sterilization cabinet 100 can retain multiple trays holding medical instruments and, because of the high venting pass through area to volume ratio, has a drying time of less than 30 minutes, and more specifically, between 10-15 minutes, and even more specifically 10 minutes. In one configuration, the sterilization cabinet 100 can hold up to 15 trays and each tray holds up to 25 lbs of material to be sterilized. In a configuration of the invention, the dry time of less than 30 minutes includes multiple trays loaded into the sterilization cabinet 100, the trays holding a total of 140 lbs or less of material to be sterilized, and in select configurations less than 15 minutes dry time.

Primary filter 108 in conjunction with filter holder 106 covers vent 104. Primary filter 108 with filter holder 106 forms a seal with the adjacent portions of sterilizing cabinet 100 such that during the operation of a sterilizing cycle, any sterilizing steam that passes through the vent 104 must then pass through primary filter 108. Primary filter 108 can be made of a very thin paper. Exemplary embodiments provide that primary filter 108 can be made of any porous material that (1) allows for the passage of sterilizing steam from sterilizing cabinet 100 and (2) prevents extraneous materials from passing through primary filter 108 and entering vent 104. Primary filter 108 is removable from sterilizing cabinet 100 and is typically replaced with a new filter following each sterilizing cycle.

Secondary filter 110 resides on top of primary filter 108 in filter holder 106. Secondary filter 110 covers primary filter 108 and forms a seal with primary filter 108 through filter holder 106 such that any sterilizing steam that passes through the vent 104 must then pass through primary filter 108 and secondary filter 110. Secondary filter 110 can be made of a very thin paper. Secondary filter 110 can be made of any porous material that (1) allows for the passage of sterilizing steam from sterilizing cabinet 100 and primary filter 108 and (2) prevents extraneous materials from passing through secondary filter 108.

Exemplary embodiments of this disclosure provide for secondary filter 110 to form a sealed periphery with primary filter 108. In another exemplary embodiment the sealed interface between the primary filter 108 and the adjacent portion of either the sterilizing cabinet 100 is independent of an interface between secondary filter 110 and primary filter 108. One exemplary arrangement provides for primary filter 108 and secondary filter 110 to be coextensive. In another exemplary embodiment primary filter 108 and secondary filter 110 have different filter properties. For instance, primary filter 108 and secondary filter 110 may filter different elements of the sterilizing agent which exits sterilizing cabinet 100 during a sterilization cycle. In an alternative exemplary embodiment primary filter 108 and secondary filter 110 have similar filter properties. Another exemplary embodiment provides that primary filter 108 and secondary filter 110 are different colors.

In yet another exemplary embodiment, primary filter 108 may be the only filter that covers vent 104. Here, primary filter 108 is removeably held or maintained in place over vent 104 by filter holder 106. In this embodiment, there is no secondary filter. Primary filter 108 forms a seal with the adjacent portions of sterilizing cabinet 100 such that during the operation of a sterilizing cycle, any sterilizing steam that passes through the vent 104 must then pass through primary filter 108. Again, in this embodiment, primary filter 108 can be made of any porous material that (1) allows for the passage of sterilizing steam from sterilizing cabinet 100 and (2) prevents extraneous materials from passing through primary filter 108 and entering vent 104. Primary filter 108 is removable from sterilizing cabinet 100 and is typically replaced with a new filter following each sterilizing cycle.

Legs 114 reside on the bottom of sterilizing cabinet 100 and provide spacing between the surface which sterilizing cabinet 100 rests and the bottom primary filter 108, secondary filter 110 and filter holder 106.

FIG. 1b provides a top view of sterilizing cabinet 100 showing vent 104 covered by filter holder 106, primary filter 108, secondary filter 110, sterilizing cabinet frame 112 and hinge 116 of filter holder 106. Hinge 116 with filter holder 106 allows a portion of filter holder 106 to swing open about hinge 116 such that primary filter 108 and secondary filter 110 can be removed independent of one another. In other words, filter holder 106 allows for secondary filter 110 to be released and removed from filter holder 106 while simultaneously maintaining primary filter's 108 seal with sterilizing cabinet 100 over vent 104.

Figure 1C:
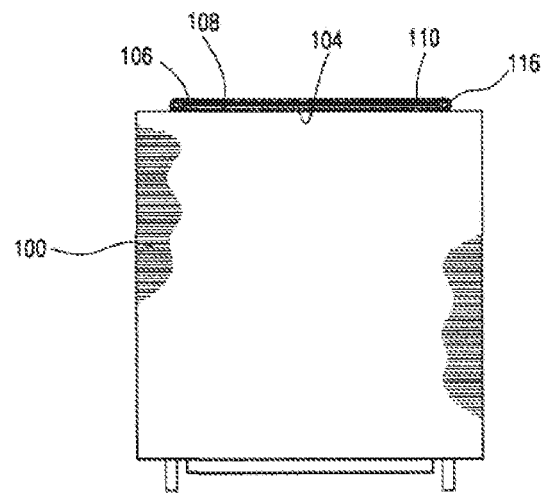
FIG. 1c is a side view of a configuration of a sterilization container such as a sterilization cabinet suitable for use in practicing exemplary embodiments of this disclosure.

FIG. 1c shows a side view of sterilizing cabinet 100 including sterilizing cabinet frame 112, vent 104, primary filter 108, secondary filter 110, filter holder 106 and hinge 116.

In exemplary embodiments sterilizing cabinet 100 may include a steam exposure indicator on either the primary filter 108 or the secondary filter 110 which designates when steam from sterilizing cabinet 100 has passed through one of the filters. An example of one such steam exposure indicator is a tape that changes colors when exposed to steam.

Figure 2A:
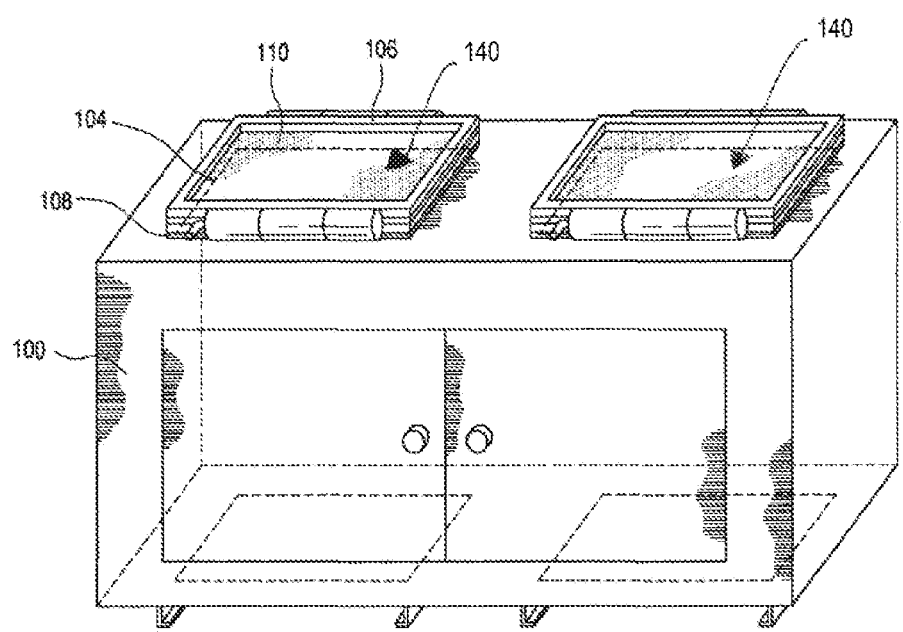
FIG. 2a is a perspective view of an alternative configuration of a sterilization container such as a sterilization cabinet suitable for use in practicing exemplary embodiments of this disclosure.

FIG. 2a provides a perspective view of sterilizing cabinet 100 with two vents 104 on the top and two vents 104 on the bottom of sterilizing cabinet 100. FIG. 2a also includes primary filters 108 occluding vents 104 and secondary filters 110 overlaying primary filters 108 with primary filters 108 and secondary filters 110 each in filter holders 106.

Figure 2B:
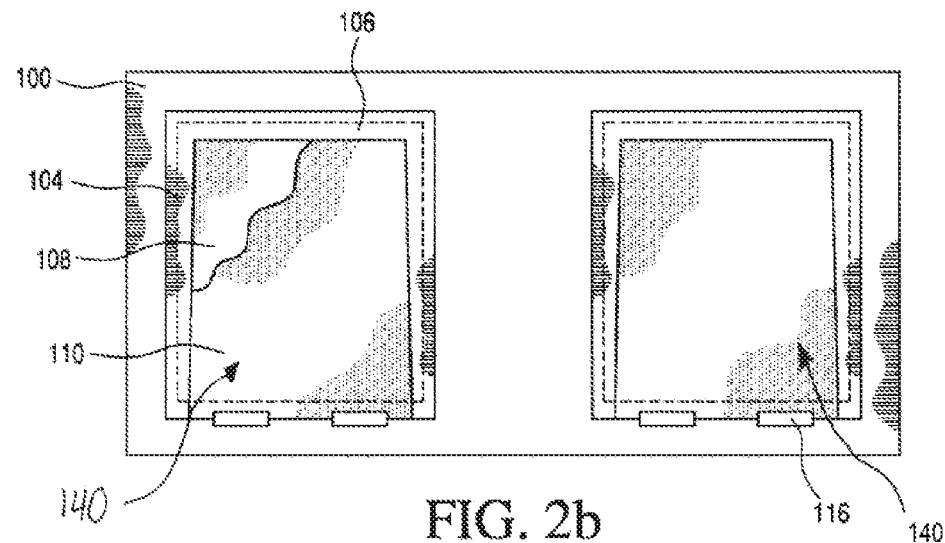
FIG. 2b is a top view of an alternative configuration of a sterilization container such as a sterilization cabinet suitable for use in practicing exemplary embodiments of this disclosure.

FIG. 2b provides a top view of sterilizing cabinet 100 with an alternative exemplary embodiment of filter holder 106. Shown in FIG. 2b are two vents 104 occluded by primary filters 108 which are also covered by secondary filters 110. In this exemplary embodiment filter holders 106 do not have a swinging hinge which allows for the individual attachment and release of primary filters 108 and secondary filters 110. In this exemplary embodiment filter holders 106 allow for independently removing primary filter 108 and secondary filter 110 through the use of a sliding mechanism. Secondary filter 110 can be removed by sliding it out of filter holder 106 while maintaining primary filter's 108 seal with sterilizing cabinet 100 around vent 104.

In another alternative exemplary embodiment, filter holder 106 again does not include a swinging hinge, but allows for the placement and removal of only primary filter 108 by a sliding mechanism. In this embodiment, there is no secondary filter 110. Only primary filter 108 in conjunction with filter holder 106 forms a sealed interface with sterilizing cabinet 100 occluding vents 104. Primary filter 108 can then be placed or removed by sliding into and out of filter holder 106.

In practice, an exemplary embodiment of a process of placing primary filter 108 and secondary filter 110 includes disposing primary filter 108 to occlude a vent 104 of sterilizing cabinet 100 and forming a first sealed interface with the sterilizing cabinet 100. The process continues by forming a second sealed interface between secondary filter 110 (or confirmatory filter) and at least a portion of one of sterilizing cabinet 100 and primary filter 108, a portion of the secondary filter 110 overlying a portion of the primary filter 108. The process can continue by passing a sterilizing agent (typically steam) through primary filter 108 and secondary filter 110 and vent 104.

Also in practice, an exemplary embodiment of a process of placing only a primary filter 108 includes disposing primary filter 108 with filter holder 106 to occlude vent 104 of sterilizing cabinet 100 creating a sealed interface with the sterilizing cabinet 100. The process can continue by passing a sterilizing agent (typically steam) through primary filter 108 and vent 104. The process can then conclude with verifying the integrity of primary filter 108 by either inspecting primary filter 108 while it covers vent 104 in filter holder 106 or after it is removed from filter holder 106. The process may be repeated if it is determined that the integrity of primary filter 108 was compromised during the sterilizing process.

Exemplary embodiments of inspecting primary filter 108 and/or secondary filter 110 can include visual inspection by either medical or nonmedical personnel, inspecting by an electronic device or machine, or inspecting through mechanical means. Exemplary embodiments of inspecting by an electronic device or machine includes any type of device that is able to scan or image the primary filter 108 and/or secondary filter 110 such that the scanned or imaged picture of the primary filter 108 and/or secondary filter 110 can be digitally viewed or examined for imperfections such as rips or cuts that would impact the integrity of the sterilization cycle. Exemplary embodiments of mechanical inspection includes any type of inspection means that physically test that the integrity of the primary filter 108 and/or secondary filter 110 has been maintained.

It should be noted that exemplary embodiments of a sterilizing agent include any substance that provides for the destruction or elimination of living organisms, which often include heat, steam, pressure, gas, plasma, irradiation, chemical compounds, and chemical vapor.

Exemplary embodiments of this process provide that the first sealed interface is separate from the second sealed interface. Additionally, failure of the second sealed interface is independent of the first sealed interface. For example, if the second sealed interface fails and leaks sterilizing steam during a sterilization cycle, the first sealed interface should remain intact and should not be affected by the failure of the second sealed interface.

Figure 3A:
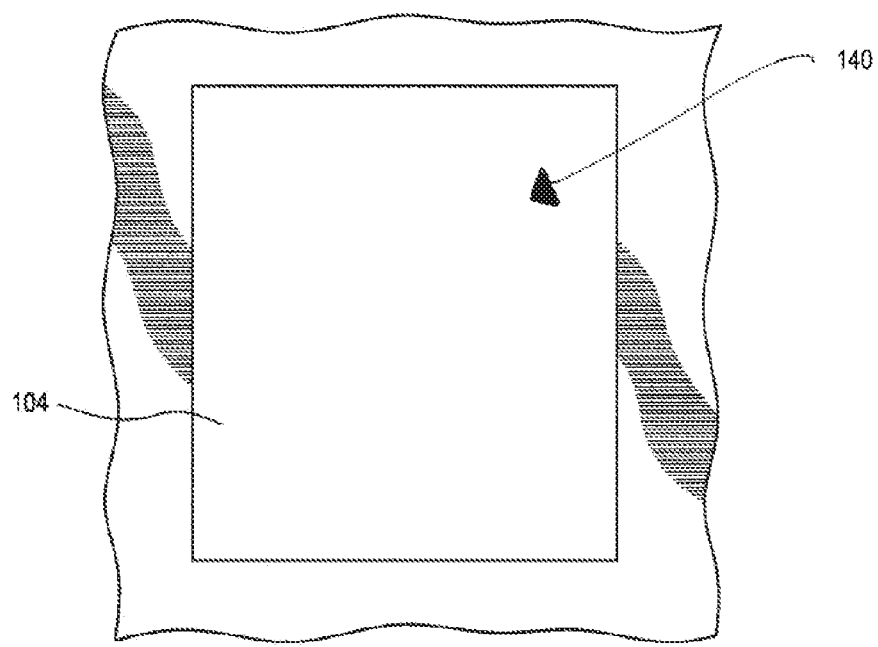
FIG. 3a is a top view of a vent of a sterilization container such as a sterilization cabinet suitable for use in practicing exemplary embodiments of this disclosure.

Referring to FIG. 3a, a top view of an exemplary vent 104 is shown. Provided is a fenestrated surface with numerous openings that allow for the passage of a sterilizing agent, such as steam from sterilizing cabinet 100 during a sterilization cycle. It can be appreciated that FIG. 3a merely represents one embodiment of vent 104 and that exemplary embodiments of vent 104 include any arrangement of holes or openings that allow for the passage of a sterilizing agent.

Figure 3B:
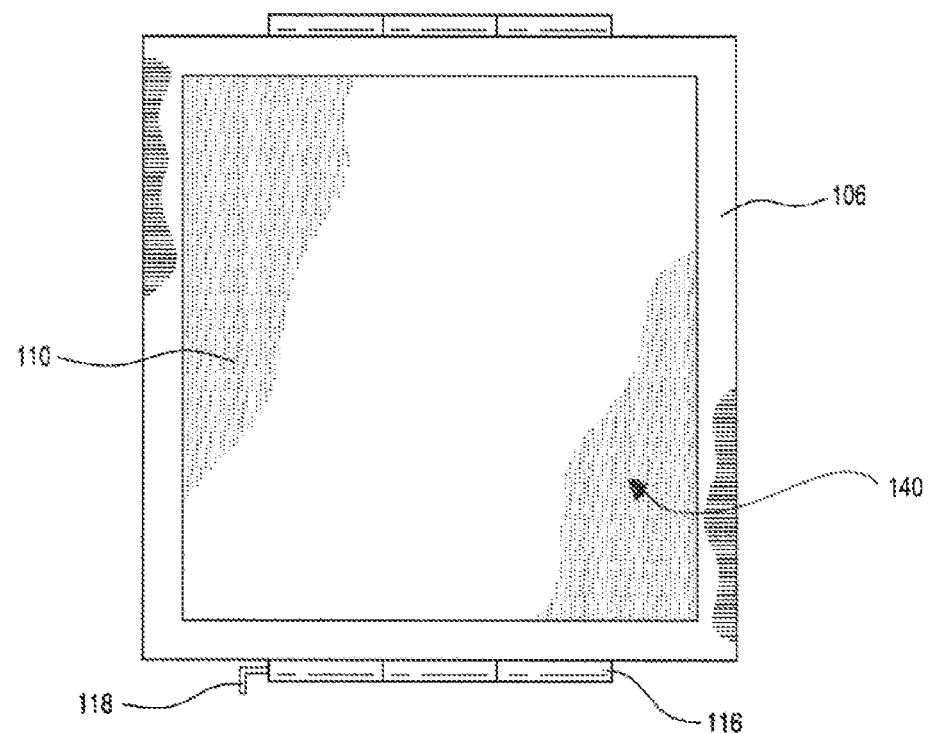
FIG. 3b is a perspective view of a filter arrangement of a sterilization container such as a sterilization cabinet for use in practicing exemplary embodiments of this disclosure.

FIG. 3b provides a top view of a filtering arrangement covering vent 104. Shown in FIG. 3b is the top portion of secondary filter 110, filter holder 106 with hinges 116 and pin 118. Exemplary embodiments of this arrangement provide for a silicon seal between filter holder 106 and primary filter 108, between filter holder 106 and secondary filter 110 and sterilizing cabinet 100. This seal serves two primary purposes. First, it forces all of the sterilizing agent that enters and exits the sterilizing cabinet 100 to pass through the filters. Second, it keeps extraneous materials from entering the sterilizing cabinet 100 through vents 104, which are covered by primary filter 108 and secondary filter 110.

It can be appreciated that exemplary embodiments of the sealed interface between the primary filter 108 and the sterilizing cabinet 100 includes both direct contact between primary filter 108 and sterilizing cabinet 100 as well as indirect contact between primary filter 108 and sterilizing cabinet 100 through the use of a sealing agent, such as caulk or an adhesive. Likewise, the sealed interface between the secondary filter and the primary filter 108 or filter holder 106 includes both direct contact between primary filter 108 or filter holder 106 as well as indirect contact through the use of a sealing agent, such as caulk or an adhesive.

Figure 4A:
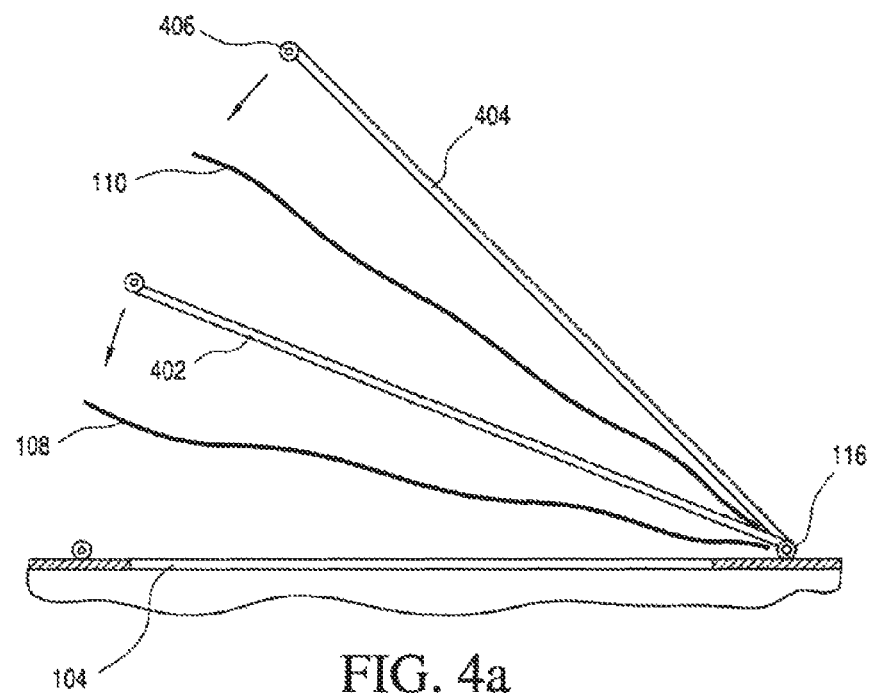
FIG. 4a is a perspective view of the movement of a filter arrangement of a sterilization container such as a sterilization cabinet for use in practicing exemplary embodiments of this disclosure.

Referring to FIG. 4a, provided is a side view of the different elements and the type of movement allowed for filter holder 106 in exemplary embodiments of this invention. Shown in FIG. 4a is the outside face of sterilizing cabinet 100, vent 104, primary filter 108, secondary filter 110, hinge 116, filter holder 106 section 402 which secures primary filter 108, and filter holder 106 section 404 which secures secondary filter 110. In this exemplary embodiment sections 402 and 404 are able to rotate about hinge 116 and can be moved from the closed position (covering vent 104) to the open position (not covering vent 104) independent of each other. For instance section 404 can be moved to the open position while section 402 remains in the closed position. However, in order for section 402 to move to the open position, section 404 must also be in the open position since it overlays section 402. Also shown in FIG. 4a are holes 406 on section 402, section 404 and on sterilizing cabinet 100. When section 402 and 404 are in the closed position, the holes 406 line-up such that a pin 118 or locking key can be inserted through the holes 406. This prevents sections 402 and 404 from opening during a sterilization cycle or at any other time when opening would be undesirable.

In alternative exemplary embodiments sections 402 and 404 are maintained or locked in the closed position through the use of a clamp or latch. It can be appreciated that exemplary embodiments of these teachings provide for any mechanism that allows sections 402 and 404 of filter holder 106 to be maintained securely in the closed position and then opened when desired.

Figure 4B:
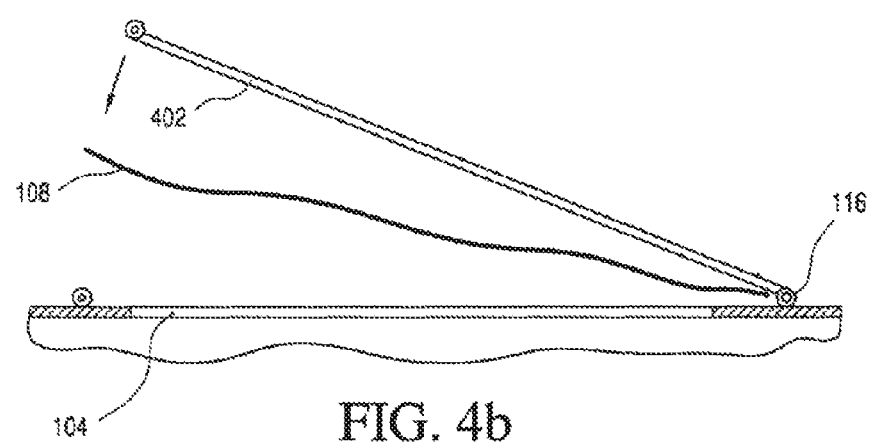
FIG. 4b is a perspective view of the movement of an alternative filter arrangement of a sterilization container such as a sterilization cabinet for use in practicing exemplary embodiments of this disclosure.

FIG. 4b provides a perspective view of the movement of an alternative filter arrangement of a sterilizing cabinet for use in practicing exemplary embodiments of this invention. Shown in FIG. 4b is the outside face of sterilizing cabinet 100, vent 104, primary filter 108, hinge 116, and filter holder 106 section 402, which secures primary filter 108. It should be noted that in this exemplary embodiment, there is only one filter (i.e., primary filter 108) and one filter holder 106 section 402. Here, filter holder 106 section 402 is able to rotate about hinge 116. It can be moved from the closed position (covering vent 104) to the open position (not covering vent 104). Also shown in FIG. 4b are holes 406 on section 402. When section 402 is in the closed position, the holes 406 line-up such that a pin 118 or locking key can be inserted through the holes 406. This prevents section 402 from opening during a sterilization cycle or at any other time when opening would be undesirable.

Figure 5A:
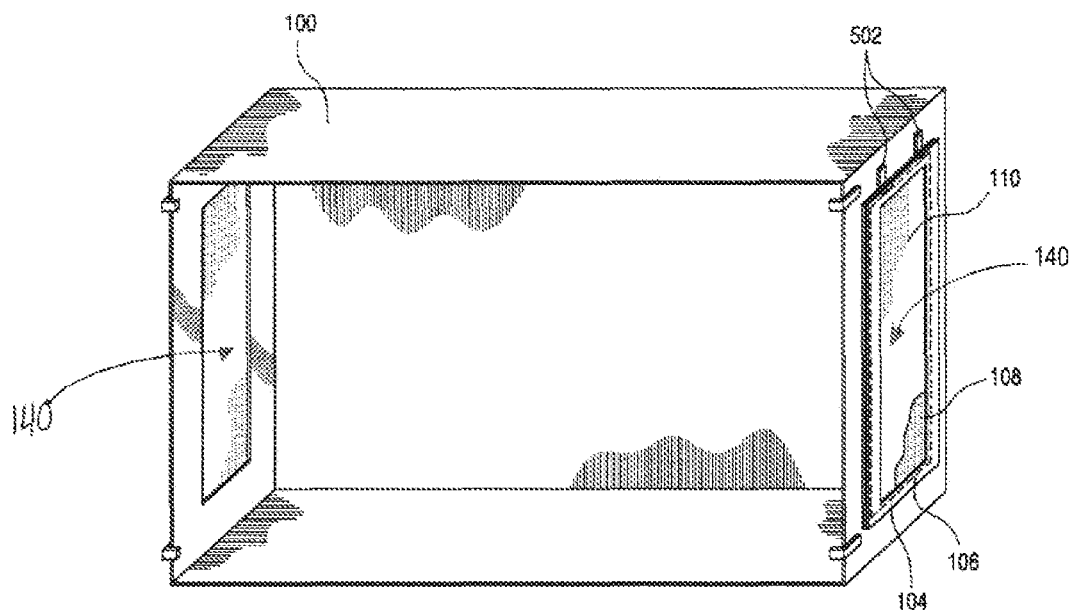
FIG. 5a is a perspective view of an alternative configuration of a sterilization container such as a sterilization cabinet suitable for use in practicing exemplary embodiments of this disclosure.

In alternative exemplary embodiments, section 402 is maintained or locked in the closed position through the use of a clamp or latch. It can be appreciated that exemplary embodiments of these teachings provide for any mechanism that allows section 402 of filter holder 106 to be maintained securely in the closed position and then opened when desired FIG. 5a provides a perspective view of an alternative arrangement of sterilization cabinet 100 with vents 104 on the sides of the cabinet. In this embodiment filter holders 110 are located on the sides of sterilization cabinet 100 with primary filter 108 and secondary filter 110. Also shown in FIG. 5a are hangers 502 from which filter holder 106, primary filter 108 and secondary filter 110 attach to sterilizing cabinet 100. It can be appreciated that exemplary embodiments of sterilization cabinet 100 include vents 104, primary filter 108, secondary filter 110 and filter holder 106 on the side of sterilization cabinet 100. As shown in FIG. 5a, the vents 104 define a venting pass through area 140 of the sterilization cabinet 100. The sterilization cabinet 100 as shown in FIG. 5a having a vent 104 on each side of the sterilization cabinet 100. For the 34 inch by 22 inch by 24 inch sterilization cabinet 100, the venting area at each end as shown in the FIG is 20 inch by 22 inch providing a venting area of 440 inch$^2$ and the total venting area is approximately 880 inch$^2$ as there are two vents 104 having the same size in the configuration of the sterilization cabinet shown in FIG. 5a. The volume of the sterilization cabinet 100, wherein the length is approximately 34 inches, the width is approximately 20, and the height is approximately 24 inches, is approximately 17,952 inch$^3$. Thus, the sterilization cabinet 100 as shown in FIG. 5a would have a venting pass through area to volume ratio of approximately 0.049 inch$^2$ per inch$^3$, wherein the venting pass through area is approximately 880 inch$^2$ compared to the volume, which is 17,952 inch$^3$. In another configuration, the sterilization cabinet 100 includes 4 similarly dimensioned vents for the cabinet of 24 inches by 22 inches by 21 inches, providing a venting pass through area of approximately 1760 inch$^2$ compared a volume of approximately 11,000 inch$^3$ providing a venting pass through area to volume ratio of approximately 0.16 inch$^2$ per inch$^3$, or 4 square inches:25 cubic inches.

These high venting pass through area to volume ratios reduce the drying time required after the sterilization cycle. The sterilization cabinet 100 can hold multiple trays holding instruments and, because of the high venting pass through area to volume ratio, have a drying time of less than 30 minutes, and more specifically, between 10-15 minutes, and even more specifically 10 minutes. These trays can each hold up to 25 lbs of material to be sterilized. In a configuration of the invention, the dry time of less than 30 minutes includes multiple trays loaded into the sterilization cabinet 100, the trays holding a total of 140 lbs or less.

Figure 5B:
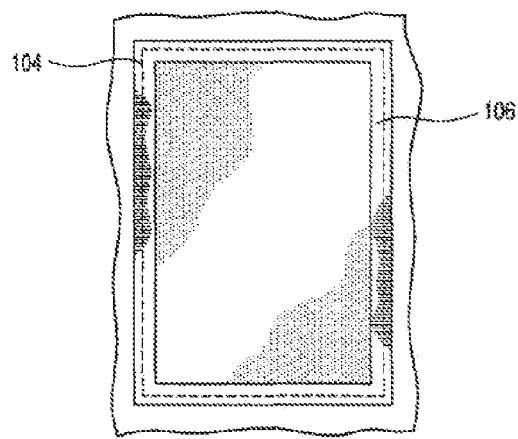
FIG. 5b is a perspective view of bottom section of a filter arrangement of a sterilization container such as a sterilization cabinet suitable for use in practicing exemplary embodiments of this disclosure.
Figure 5C:
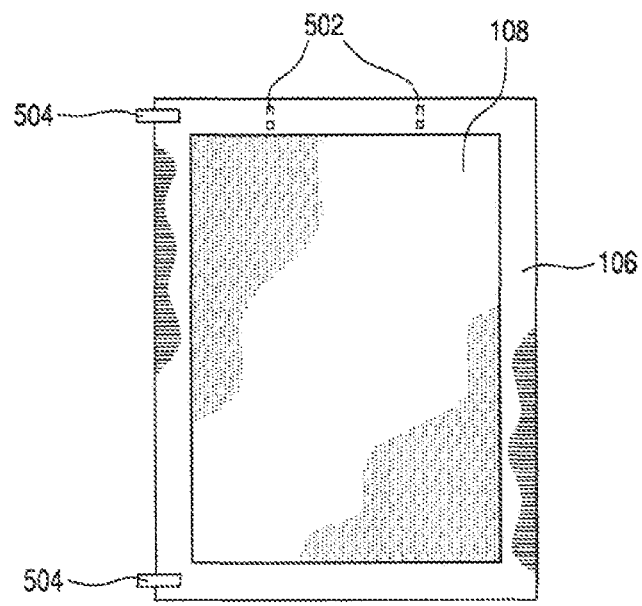
FIG. 5c is a perspective view of a middle section of a filter arrangement of a sterilization container such as a sterilization cabinet suitable for use in practicing exemplary embodiments of this disclosure.
Figure 5D:
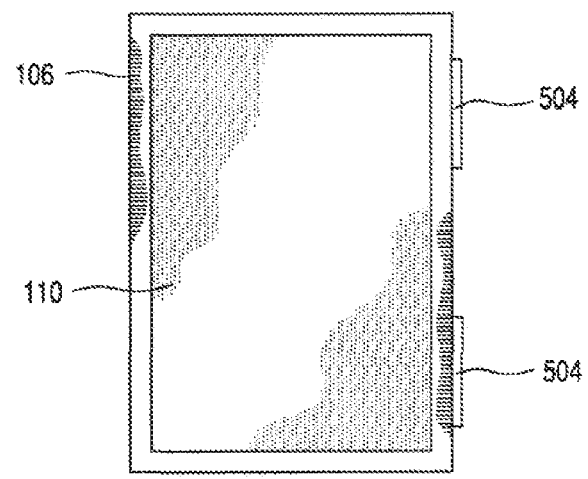
FIG. 5d is a perspective view of top section of a filter arrangement of a sterilization container such as a sterilization cabinet suitable for use in practicing exemplary embodiments of this disclosure.

FIG. 5b shows a front facing view of vent 104 with filter holder 106 overlaying vent 104 on sterilizing cabinet 100. In this embodiment filter holder 106 is sized such its edges completely cover the portions surrounding vent 104. FIG. 5c shows primary filter 108 and filter holder 106 overlaying vent 104. Primary filter 108 as shown hangs from hangers 502 and attaches to filter holder 106 by clamps 504.

Figure 6A:
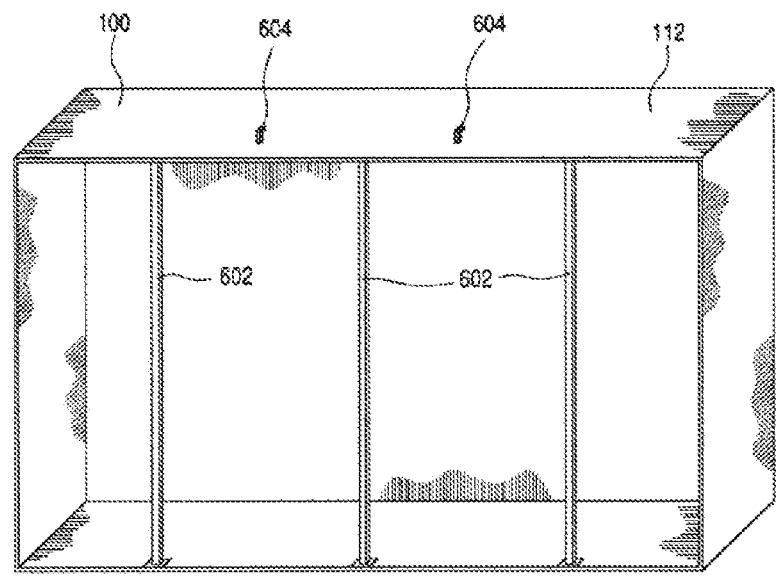
FIG. 6a is a perspective view of an alternative sterilization container such as a sterilization cabinet suitable for use in practicing exemplary embodiments of this disclosure.
Figure 6B:
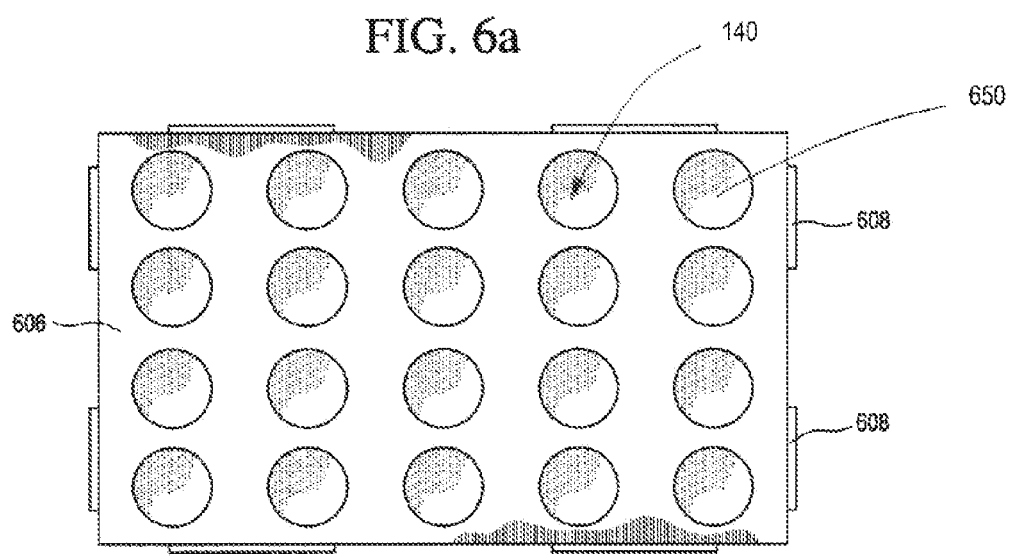
FIG. 6b is a front view of an alternative filter arrangement of a sterilization container such as a sterilization cabinet suitable for use in practicing exemplary embodiments of this disclosure.
Figure 6C:
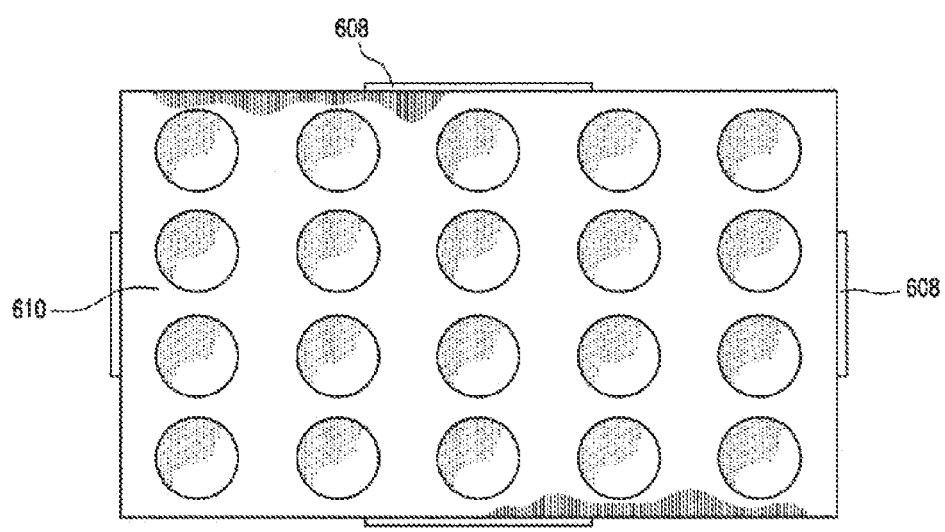
FIG. 6c is a front view of the top portion of an alternative filter arrangement of a sterilization container such as a sterilization cabinet suitable for use in practicing exemplary embodiments of this disclosure.

In yet another exemplary embodiment, as shown in FIGS. 6a-6c, the sterilization cabinet 100 includes sterilization cabinet frame 112, bars 602 and hooks 604. In this configuration, there is no front side of sterilization cabinet 100 in front of bars 602. It should be appreciated that exemplary embodiments of sterilizing cabinet 100 also include embodiments of sterilization cabinet 100 that do not contain bars 602. In yet another exemplary embodiment of sterilization cabinet 100, bars 602 are removeable such that bars 602 can be removeably affixed to sterilization cabinet 100 when desired. FIG. 6b illustrates filter door 606 which contains primary filter 106. In exemplary embodiments filter door 606 covers the front opening of sterilizing cabinet 100 in FIG. 6a. Filter door 606 clamps onto sterilization cabinet 100 with clamps 608. Bars 602 prevent the contents of sterilization cabinet 100 (typically a tray containing instruments for sterilization) from ripping or breaking primary filter 108 and secondary filter 110.

FIG. 6c illustrates a second filter door 610, which attaches to filter door 606 and sterilizing cabinet 100 with the use of clamps 608. In this configuration, it can be appreciated that clamps 608 on filter door 610 fit into the spacing between clamps 608 on filter door 606. This arrangement prevents the clamps 608 from filter door 606 from interfering with clamps 608 from filter door 610. Additionally, since filter door 610 is attached independently from filter door 606, secondary filter 110 can be removed with filter door 610 after a sterilization cycle has completed without disturbing filter door's 606 seal with sterilization cabinet 100. Each filter door 606, 610 includes a plurality of holes or openings 650 for the passage of sterilizing steam or heat. Although holes or openings are shown, it should be appreciated that any type of opening can be used, including but not limited to holes, slits, diamonds, or fenestrated openings as long as the available area for the ingress and egress of a gas to and from the interior volume of the sterilizing cabinet 100 provides the desired venting pass through area to volume ratio. Further, it should be appreciated that, although the plurality of holes 650 of filter door 606 and filter door 610 in the configuration shown in FIGS. 6b and 6c will align, such alignment is not necessary. The venting pass through area to volume ratio is based on the venting pass through area 140 of the primary filter 108 and first door 606 and not both doors. It should be appreciated that the gas passing through the secondary filter 110 will be dispersed into a flow path that may be different than the flow path through the holes 650 of the first door 606.

In this embodiment, filter door 606 forms a seal with sterilization cabinet 100 at the edges of the open portion of the sterilization cabinet frame 112, such that any sterilizing steam that enters or exits sterilizing cabinet 100 during a sterilization cycle must pass through filter door 606 and primary filter 106. Likewise, filter door 610 forms a seal with filter door 606 such that any sterilizing steam that exits sterilizing cabinet 100 and primary filter 108 must pass through filter door 610 and secondary filter 110. As shown in FIG. 6b, the filter door 606 includes holes or openings 650 and defines a venting pass through area 140 of the sterilization cabinet 100. The sterilizing cabinet 100 as shown in FIG. 6b having 20 holes within the door 606 having dimensions of approximately 34 inches by 24 inches includes a venting pass through area of approximately 240 inch$^2$ based on each hole having an area of approximately 12 inch$^2$. The total volume of the sterilization cabinet 100, wherein the length is approximately 34 inches, the width is approximately 22 inches, and the height is approximately 24 inches, is approximately 17,952 inches$^3$. Thus, the sterilization cabinet 100 as shown in FIG. 6b would have a venting pass through area to volume ratio of approximately 0.01 inch$^2$ per inch$^3$.

Alternatively, for the sterilization container of FIG. 6b, being 24 inch by 11 inch by 11 inch, the venting pass through area to volume ratio of approximately 0.08 inch$^2$ per inch$^3$ is obtained, that is 2 square inches per 25 cubic inches. Similarly, for the sterilization container of FIG. 6b, being 34 inch by 30 inch by 30 inch, the venting pass through area to volume ratio of approximately 0.008 inch$^2$ per inch$^3$ is obtained.

Exemplary embodiments of sterilization cabinet 100 can include one or more vents so long as the venting pass through area to volume ratio is equal to or greater than 0.008 inch$^2$ per inch$^3$, or 1 square inch:125 cubic inches, and in select configurations between 0.02-0.2 inch$^2$ per inch$^3$, or between 1 square inch:50 cubic inches and 1 square inch:5 cubic inches, and in further configurations between 0.16-0.2 inch$^2$ per inch$^3$, or 4 square inches:25 cubic inches and 1 square inch:5 cubic inches.

The high venting pass through area to volume ratio reduces the drying time required after the sterilization cycle. The sterilization cabinet 100 can hold multiple trays holding instruments and, because of the venting pass through area to volume ratio, have a drying time of less than 30 minutes, and more specifically, between 10-15 minutes, and even more specifically 10 minutes. In select configurations, the drying time can be as little as 5 minutes. In one configuration, the sterilization cabinet 100 holds up to 15 trays, each tray holding up to 25 lbs. In a configuration of the disclosure, the drying time of less than 30 minutes includes multiple trays loaded into the sterilization cabinet 100, the trays holding a total of 140 lbs or less.

Figure 7A:
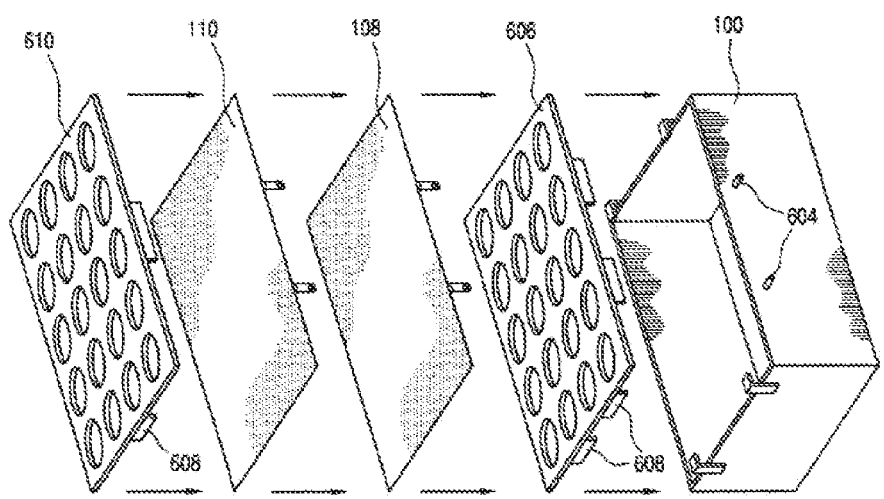
FIG. 7a is a perspective view of the separated elements of an alternative filter arrangement of a sterilization container such as a sterilization cabinet suitable for use in practicing exemplary embodiments of this disclosure.

FIG. 7a depicts a perspective view of the construction of the alternative arrangement sterilizing cabinet 100 from FIGS. 6a, 6b and 6c. As shown filter door 606 with clamps 608 attach around the frame of sterilizing cabinet 100. Primary filter 108 is placed on top of filter door 606 and attaches to sterilizing cabinet 100 at hooks 604. Secondary filter 110 is placed on top of primary filter 108 and also attaches to sterilizing cabinet 100 at hooks 604. Filter door 610 is then placed on top of secondary filter 110 and attached to sterilizing cabinet 100 with clamps 608. As illustrated in FIG. 7a, exemplary embodiments of filter doors 606 and 608 contain numerous holes or openings along their surface, and allow for the passage of sterilizing steam. Exemplary embodiments of filter doors 606 and 608 are able to be fully or partially separable from sterilizing cabinet 100. It should also be appreciated that filter doors 606 and 608 can optionally employ the use of a hinge, clamp, clasp or the like as the mechanism for removing and replacing filter doors 606 and 608 on sterilizing cabinet 100.

Figure 7B:
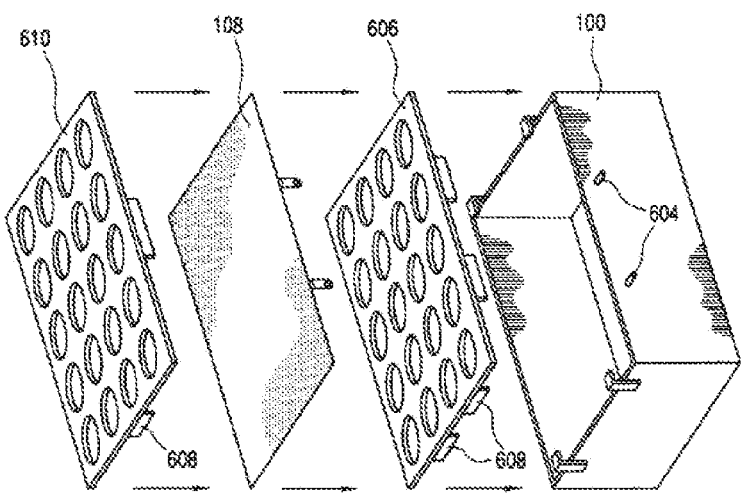
FIG. 7b is a perspective view of the separated elements of another filter arrangement of a sterilization container such as a sterilization cabinet suitable for use in practicing exemplary embodiments of this invention.

FIG. 7b depicts an alternative perspective view of the construction of another alternative arrangement sterilizing cabinet 100. As shown filter door 606 with clamps 608 attach around the frame of sterilizing cabinet 100. Primary filter 108 is placed on top of filter door 606 and attaches to sterilizing cabinet 100 at hooks 604. In this embodiment, there is only a single filter and no secondary filter. Primary filter 108 creates a sealed interface with filter door 606 such that extraneous materials cannot enter sterilizing cabinet 100. Filter door 610 is then placed on top of primary filter 108 and attached to sterilizing cabinet 100 with clamps 608.

In another exemplary embodiment, primary filter 108 does not create a sealed interface with filter door 606 until filter door 610 is placed on top of primary filter 108 and filter door 606. In this embodiment, a sealed interface between filter door 610 and primary filter 108, and a sealed interface between filter door 606 or sterilizing cabinet 100 and primary filter 108 is only created when filter door 610 is attached or affixed to sterilizing cabinet 100. As illustrated in FIG. 7b, exemplary embodiments of filter doors 606 and 608 which contain numerous holes or openings along their surface, which allow for the passage of sterilizing steam.

It should be noted that exemplary embodiments of FIG. 7b provide that filter door 610 can be removed from sterilizing cabinet 100, primary filter 108 and filter door 606 without disturbing or disrupting the sealed interface between primary filter 108 and inter door 606. This win prevent the possibility of extraneous materials from entering sterilizing cabinet 100 after a sterilizing cycle when filter door 610 is removed in order to either allow primary filter 108 and filter door 606 to be removed as well or for primary filter 108 to be inspected to verify that it maintained its integrity during the sterilizing cycle.

In an alternative exemplary embodiment, the sealed interface between filter door 610 and primary filter 108, and the sealed interface between filter door 606 or sterilizing cabinet 100 and primary filter 108 is broken or can be broken when filter door 610 is removed from sterilizing cabinet 100, primary filter 108, and filter door 606. In yet another exemplary embodiment, the sealed interface between filter door 610 and primary filter 108, and the sealed interface between filter door 606 or sterilizing cabinet 100 and primary filter 108 is only created and thereafter maintained when sterilizing cabinet 100 along with filter door 610, filter door 606 and primary filter 108 are exposed to a sterilization cycle. Exemplary embodiments of sterilizing cabinet 100 as depicted in FIG. 7b are able to maintain the sealed interface between filter door 610 and primary filter 108, and the sealed interface between filter door 606 or sterilizing cabinet 100 and primary filter 108 for an extended period of time following being exposed to a sterilization cycle, such as sterilizing steam. For example, the sealed interface may be able to remain intact for as long as 30-90 days. In other exemplary embodiments the sealed interface may only remain intact for a matter of hours.

Figure 8A:
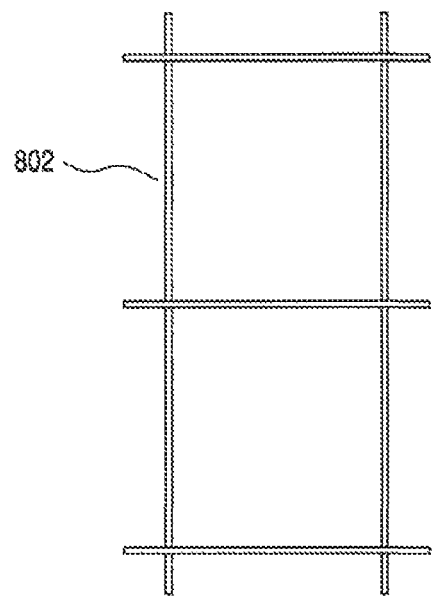
FIG. 8a is a top view of a spacer suitable for use in practicing exemplary embodiments of this disclosure.
Figure 8B:
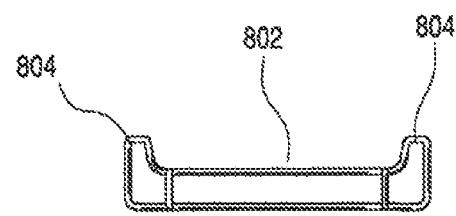
FIG. 8b is a side view of a spacer suitable for use in practicing exemplary embodiments of this disclosure.
Figure 8C:
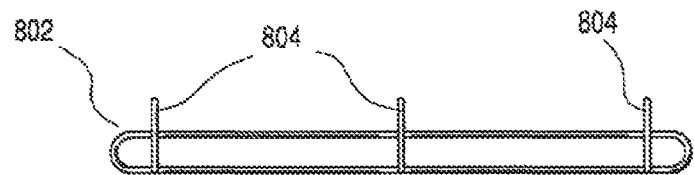
FIG. 8c is another side view of a spacer suitable for use in practicing exemplary embodiments of this disclosure.

Referring to FIGS. 8a, 8b and 8c, provided are different views of a spacer 802 for use in exemplary embodiments of sterilizing cabinet 100. In this embodiment spacer 802 has a wire frame and is sized such that when it is placed inside sterilizing cabinet 100 it does not move. The length and width of spacer 802 closely matches the dimensions (i.e., the depth and width) of the inside of sterilizing cabinet 100. This prevents spacer 802 from sliding or moving inside sterilizing cabinet 100 during a sterilization cycle or while sterilizing cabinet 100 is being moved. It should be appreciated that spacer 802 is shaped such that there are dividers or lips 804 along the edges of spacer 802 and at spacer's 802 midsection. The dividers or lips 804 are illustrated most clearly in FIGS. 8b and 8c. In practice, sterilizing trays can be placed on top of spacer 802 prior to a sterilization cycle. In order to ensure that all of the contents of sterilizing cabinet 100 are sterilized, it is advantageous to prevent sterilizing trays from touching. This can obscure portions of the sterilizing trays or their contents from the sterilizing steam. As such, the dividers or lips 804 provide a physical barrier between sterilizing trays creating a minimum separation between the trays. This allows the passage sterilizing steam during a sterilization cycle throughout sterilizing cabinet 100. Additionally, the dividers or lips 804 of spacer 802 are sized such that they accommodate the shape and size of sterilizing trays and thus substantially prevent lateral movement (e.g., sliding) of sterilizing trays when not desired before, during or following a sterilization cycle.

Figure 9A:
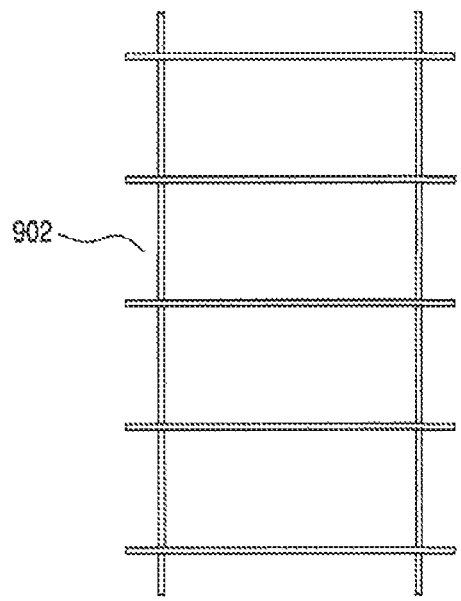
FIG. 9a is a top view of an alternative spacer suitable for use in practicing exemplary embodiments of this disclosure.
Figure 9B:
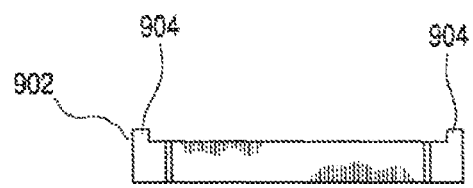
FIG. 9b is a side view of an alternative spacer suitable for use in practicing exemplary embodiments of this disclosure.
Figure 9C:
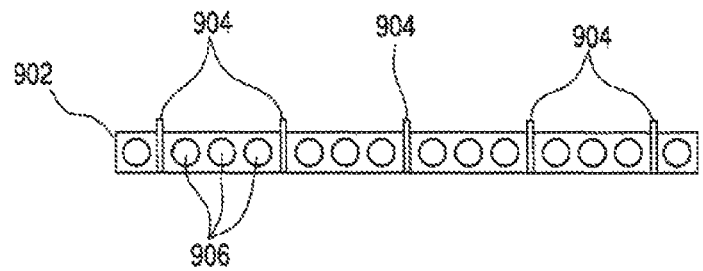
FIG. 9c is another side view of an alternative spacer suitable for use in practicing exemplary embodiments of this disclosure.

FIGS. 9a, 9b and 9c illustrate an alternative spacer 902 for use inside exemplary embodiments of sterilizing cabinet 100. In this embodiment spacer 902 is made of thin sheets (e.g., metal or aluminum alloys) with holes 906 throughout the length of the sheets. In this embodiment spacer 902 is sized such that when it is placed inside sterilizing cabinet 100 it does not move. The length and width of spacer 902 closely matches the dimensions (i.e., the depth and width) of the inside of sterilizing cabinet 100. This prevents spacer 902 from sliding or moving inside sterilizing cabinet 100 during a sterilization cycle or while sterilizing cabinet 100 is being moved. Spacer 902 is shaped such that there are dividers or lips 904 along the edges of spacer 902 and throughout spacer's 902 mid-section. The dividers or lips 904 can be viewed most clearly in FIGS. 9b and 9c. In practice, sterilizing trays can be placed on top of spacer 902 prior to a sterilization cycle. In order to ensure that all of the contents of sterilizing cabinet 100 are sterilized, it is advantageous to prevent sterilizing trays from touching. This can obscure portions of the sterilizing trays or their contents from the sterilizing steam. As such, the dividers or lips 904 provide a physical barrier between sterilizing trays creating a minimum separation between the trays. This allows the passage sterilizing steam during a sterilization cycle throughout sterilizing cabinet 100. Holes 906 encompasses any variation of openings that allow for the passage of sterilizing steam during a sterilization cycle yet maintaining structural integrity of spacer 902 to carry the weight of the sterilizing trays and their contents.

Exemplary embodiments of spacers 802 and 902 provide for the spacer to be fenestrated. In another exemplary embodiment spacers 802 and 902 are not reusable but are disposable and can only be sterilized once. In another exemplary embodiment spacers 802 and 902 provide vertical spacing between trays by at least 0.1 to 5 inches. In yet another exemplary embodiment, spacers 802 and 902 provide vertical spacing between trays by at least 10 to 26 inches.

Figure 10:
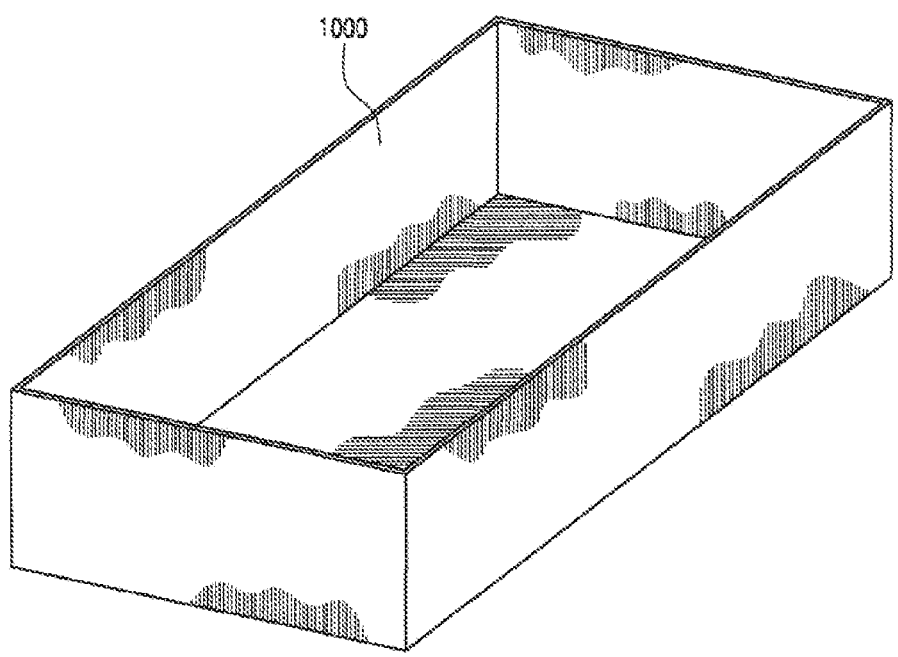
FIG. 10 is a perspective view of a sterilizing tray suitable for use in practicing exemplary embodiments of this disclosure.

FIG. 10 provides an exemplary embodiment of a sterilizing tray for practicing exemplary embodiments of this disclosure. For the purposes of this disclosure, the terms tray and pan are interchangeable and refer to an instrument with a closed rigid bottom and sides and an open top. Illustrated in FIG. 10 is sterilizing tray 1000 with an open top and a closed rigid bottom and sides. Sterilizing tray 1000 can be made of any material that can be sterilized (sterilizable) and is rigid enough such that it can hold items to be sterilized. For example sterilizing tray 1000 can be made of metals or metal alloys. Exemplary embodiments of sterilizing tray 1000 provide for a tray that has dimensions that make it suitable for use with spacers 802 and 902 and sterilizing cabinet 100. Exemplary embodiments of sterilizing tray 1000 also includes trays with holes, slits, fenestrations or other openings that allow for the passage of a sterilizing agent during a sterilization cycle.

In an exemplary embodiment in accordance of the present disclosure, spacers 802 or 902 can be used in conjunction with sterilizing cabinet 100 and one or more sterilizing trays 1000 during a sterilization cycle. in this embodiment the one or more sterilizing trays 1000 are of the shape and size so that they can be retained within sterilizing cabinet 100 and fit between the dividers 904 in spacers 902.

Figure 11:
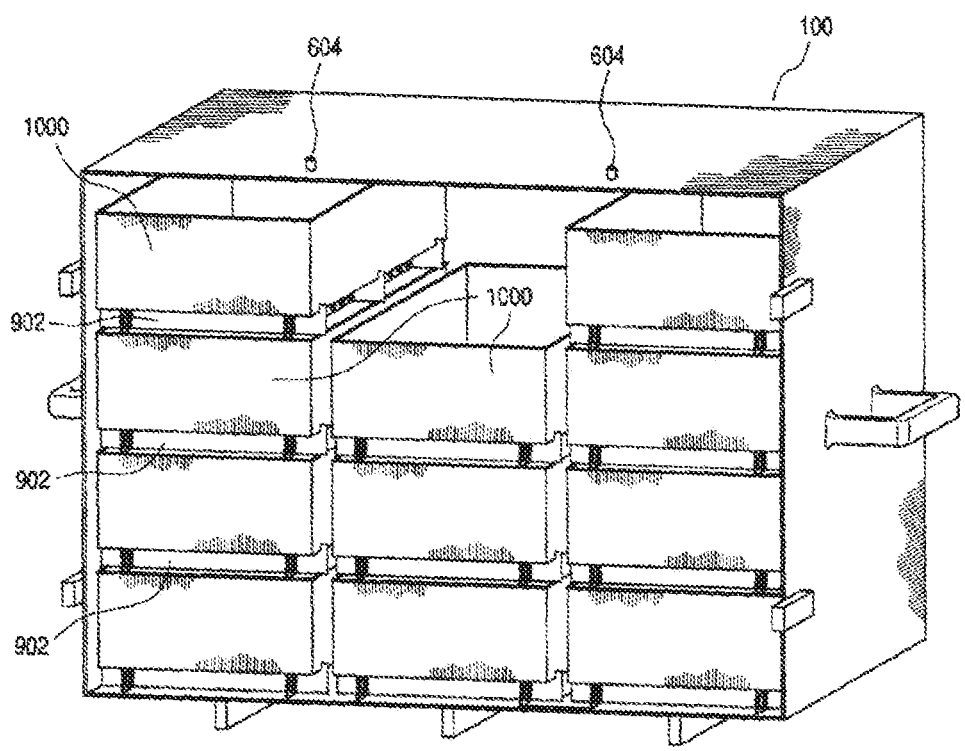
FIG. 11 is a perspective view of a sterilization container such as a sterilization cabinet suitable for use in practicing exemplary embodiments of this disclosure.

In practice, as shown in FIG. 11, a first tray is placed in sterilizing cabinet 100 on a spacer 902. On top of the first tray 1000 spacer 902 is then placed. Next, a second tray 1000 is placed in sterilizing cabinet 100 on top of spacer 902. The spacer 902 vertically separates the first tray 1000 from the second tray 1000 in sterilizing cabinet 100. Spacer 902 also inhibits lateral displacement of the first and second tray 1000 through the use of the dividers and lips 904. The spacers 902 play the important role of allowing sterilizing steam to pass between the sterilizing trays 1000 during a sterilization cycle. It can be appreciated that exemplary embodiments include the addition of more sterilizing trays 1000 and spacers 902 arranged in accordance with the first and second sterilizing trays described. Exemplary embodiments of spacers 902 provide space between the first and second tray 1000 by at least 10 to 26 inches.

Figure 12:
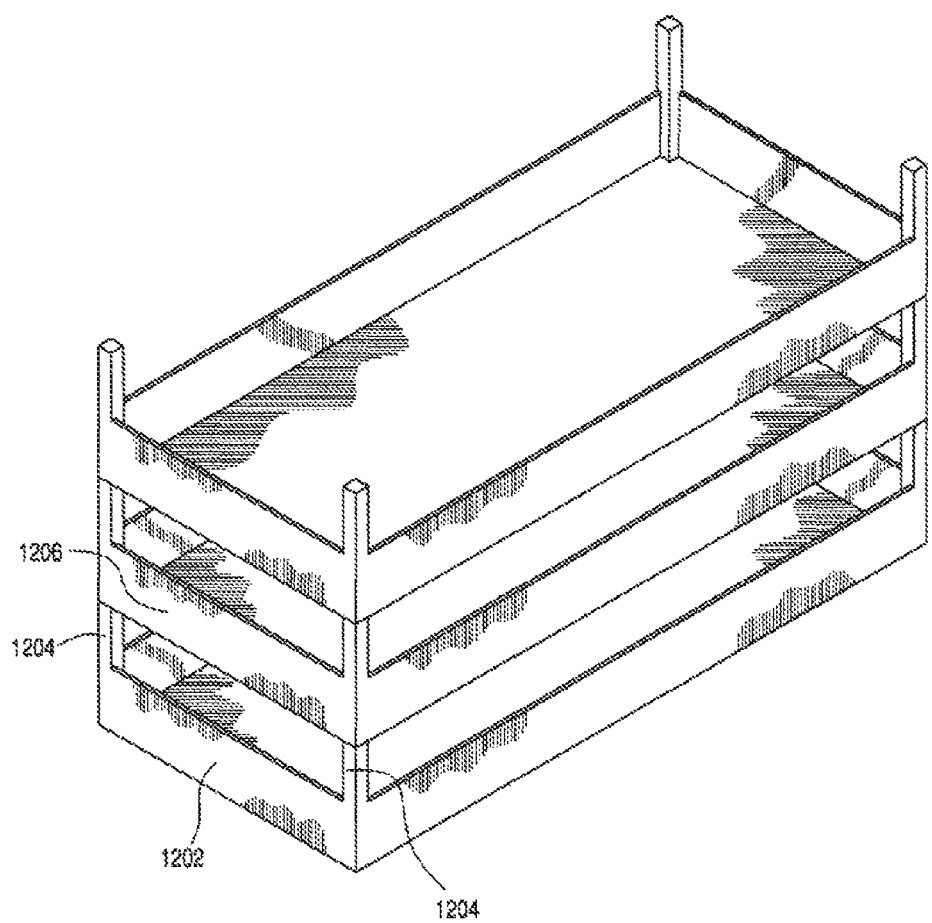
FIG. 12 is a perspective view of a pan assembly suitable for use in practicing exemplary embodiments of this disclosure.

Exemplary embodiments of these teachings also provide for a sterilizable pan assembly for sterilization within sterilizing cabinet 100. The sterilizable pan assembly as shown in FIG. 12 illustrates a first sterilizable pan 1202 with an open top and a closed bottom. Protruding from the top of the first sterilizable pan 1202 are four legs 1204. Exemplary embodiments of the first sterilizable pan 1202 also includes legs 1204 that protrude from the bottom of the first sterilizable pan 1202. These legs are configured to releasably attach to a portion of a second sterilizable pan 1206. Legs 1204 when attached to the second sterilizable pan 1206 maintain a vertical spacing between the bottom of the first sterilizable pan 1202 and the top of the second sterilizable pan 1206. In one exemplary embodiment the vertical spacing is at least 0.1 to 5 inches. In another exemplary embodiment, the vertical spacing is such that it allows for the passage of a sterilizing steam from a sterilization cycle of sterilizing cabinet 100. Exemplary embodiments of this pan assembly are configured such that they can be used within sterilizing cabinet 100 during a sterilization cycle.

Figure 13A:
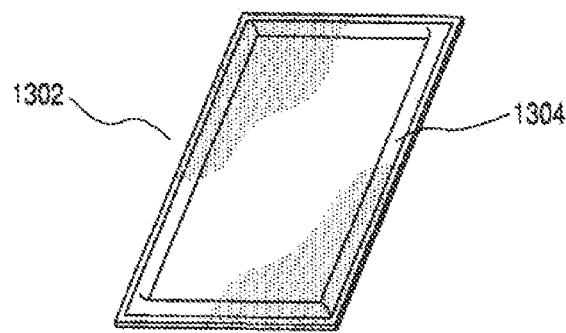
FIG. 13a is a perspective view of a filter suitable for use in practicing exemplary embodiments of this disclosure.
Figure 13B:
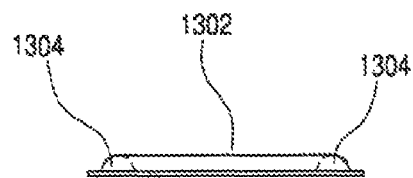
FIG. 13b is a side view of a filter suitable for use in practicing exemplary embodiments of this disclosure.

Referring to FIG. 13a, provided is an exemplary embodiment of a filter suitable for use in practicing exemplary embodiments of this disclosure. Shown in FIG. 13a is filter 1302 with a beaded edge 1304. Filter 1302 can be made of any type of porous paper or cellulose type material. In other embodiments, filter 1302 is made of polymeric substances, such as polypropylene. Filter 1302 is required to be both porous and dense enough to allow the passage of a sterilizing agent, such as steam, through its membrane, but also resilient enough to not rip or tear during a sterilizing cycle or during insertion clamping into a filter holder. In another embodiment, filter 1302 is both porous and less resilient such that filter 1302 can be ripped or torn during use in a sterilizing cycle or with filter holder 106. The beaded edge 1304 creates a raised portion along the edges of the filter 1302 as shown in FIG. 13b. This enables filter 1302 to create a sealed interface when used with sterilizing cabinet 100 and filter holder 106 over vents 104. in an alternative embodiment, beaded edge 1304 is placed inside the edge of filter 1302 rather than on the edge of filter 1302 such that there is a space between the edge of filter 1302 and beaded edge 1304.

Exemplary embodiments of filter 1302 provide for filter 1302 to have different densities along given cross-sections of the face of filter 1302. For instance, filter 1302 may have a higher density along its periphery and a lower density towards its center. Exemplary embodiments of filter 1302 also provide for filter 1302 to have different thicknesses throughout its cross-section. The different thicknesses of filter 1302 provide different lengths of travel for sterilizing agents, which pass through filter 1302.

Exemplary embodiments of filter 1302 have a length and width that corresponds to the size of vents 104 of sterilizing cabinet 100 and filter holder 106. Additionally, the thickness of beaded edge 1304 corresponds to a size that is able to fit between sterilizing cabinet 100 and filter holder 106 or between the different sections of filter holder 106. The thickness of beaded edge 1304 is also such that the sealed interface between sterilizing cabinet 100 and filter holder 106 or between the different sections of filter holder 106 prevents extraneous materials from entering sterilizing cabinet 100 and forces all of the sterilizing agent that enters and exits sterilizing cabinet 100 to pass through filter 1302.

The beaded edge 1304 can be made of a silicone based material or any other material that can create a sealed interface between sterilizing cabinet 100 or filter holder 106 and filter 1302. The beaded edge 1304 also is required to be able to withstand high temperatures in excess of 275 degrees without compromising its structural or chemical integrity. Exemplary embodiments of filter 1502 have a length and width that corresponds to the size of vents 104 of sterilizing cabinet 100 and filter holder 106.

Figure 14A:
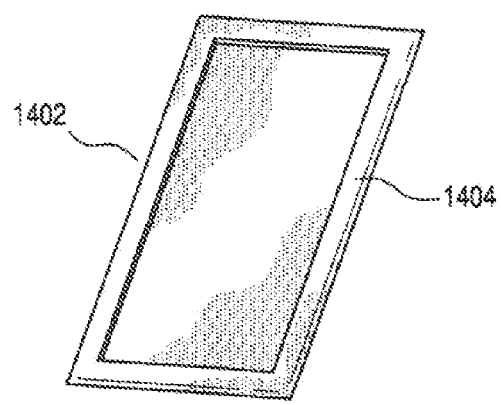
FIG. 14a is a perspective view of an alternative filter suitable for use in practicing exemplary embodiments of this disclosure.

FIG. 14a provides an alternative exemplary embodiment of a filter suitable for use in practicing exemplary embodiments of this disclosure. Shown in FIG. 14a is filter 1402 with folded edge 1404. Filter 1402 can be made of any type of porous paper or cellulose type material. In other embodiments filter 1402 is made of polymeric substances, such as polypropylene. Filter 1402 is required to be porous enough to allow the passage of a sterilizing agent, such as steam through its membrane, but also resilient enough to not rip or tear during a sterilizing cycle or during insertion/clamping into a filter holder 106. In another embodiment filter 1402 is both porous and less resilient such that filter 1402 can be ripped or torn during use in a sterilizing cycle or with filter holder 106.

Figure 14B:
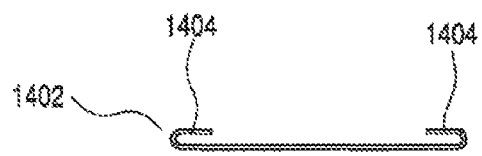
FIG. 14b is a side view of an alternative filter suitable for use in practicing exemplary embodiments of this disclosure.

The folded edge 1404 is created by the edges of filter 1402 folded onto itself thereby creating a thicker membrane along the edges of filter 1402 as shown in FIG. 14b. The thicker membrane of folded edge 1404 provides for a better-sealed interface between sterilizing cabinet 100 and filter holder 106 as there is less likelihood that spaces can be created between filter 1402 and sterilizing cabinet 100 which would allow for the passage of sterilizing steam or extraneous materials. Exemplary embodiments of filter 1402 have a length and width that corresponds to the size of vents 104 of sterilizing cabinet 100 and filter holder 106.

Additionally, the thickness of folded edge 1404 corresponds to a size that is able to fit between sterilizing cabinet 100 and filter holder 106 or between the different sections of filter holder 106. The thickness of edge 1404 is also such that the sealed interface between sterilizing cabinet 100 and filter holder 106 or between the different sections of filter holder 106 prevents extraneous materials from entering sterilizing cabinet 100 and forces all of the sterilizing agent that enters and exits sterilizing cabinet 100 to pass through filter 1402.

Figure 15A:
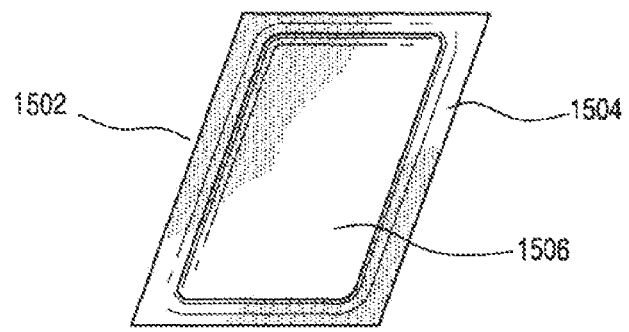
FIG. 15a is a perspective view of another filter suitable for use in practicing exemplary embodiments of this disclosure.

Referring to FIG. 15a, provided is another exemplary embodiment of a filter suitable for use in exemplary embodiments of this disclosure. Shown in FIG. 15a is filter 1502, filter edge 1504 and filter center 1506. Filter 1502 can be made of any type of porous paper or cellulose type material. In other embodiments filter 1502 is made of polymeric substances, such as polypropylene. Filter 1502 is required to be porous enough to allow the passage of a sterilizing agent, such as steam through its membrane, but also resilient enough to not rip or tear during a sterilizing cycle or during insertion/clamping into a filter holder 106. In another embodiment filter 1502 is both porous and less resilient such that filter 1502 can be ripped or torn during use in a sterilizing cycle or with filter holder 106.

Figure 15B:
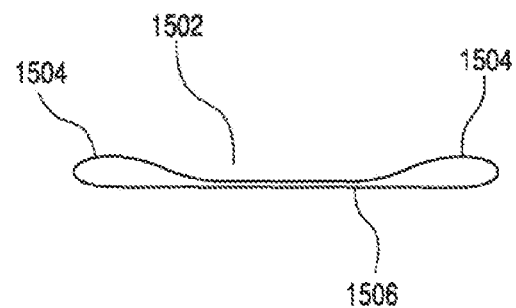
FIG. 15b is a side view of another filter suitable for use in practicing exemplary embodiments of this disclosure.

Filter edge 1504 provides for a thicker portion of filter 1502 as shown in FIG. 15b. The thickness of filter edge 1504 enables filter 1502 to make a better compressed sealed interface with sterilizing cabinet 100 and filter holder 106. Exemplary embodiments of filter 1502 have a length and width that corresponds to the size of vents 104 of sterilizing cabinet 100 and filter holder 106. Additionally, the thickness of edge 1504 corresponds to a size that is able to fit between sterilizing cabinet 100 and filter holder 106 or between the different sections of filter holder 106. The thickness of edge 1504 is also such that the sealed interface between sterilizing cabinet 100 and filter holder 106 or between the different sections of filter holder 106 prevents extraneous materials from entering sterilizing cabinet 100 and forces all of the sterilizing agent that exits sterilizing cabinet 100 to pass through center 1506 of filter 1502.

Center 1506 of filter 1502 includes all of the area of filter 1502 other than edge 1504 that is of normal or customary thickness for a filter that allows the passage of sterilizing steam, but prevents the passage of other extraneous materials.

Figure 16:
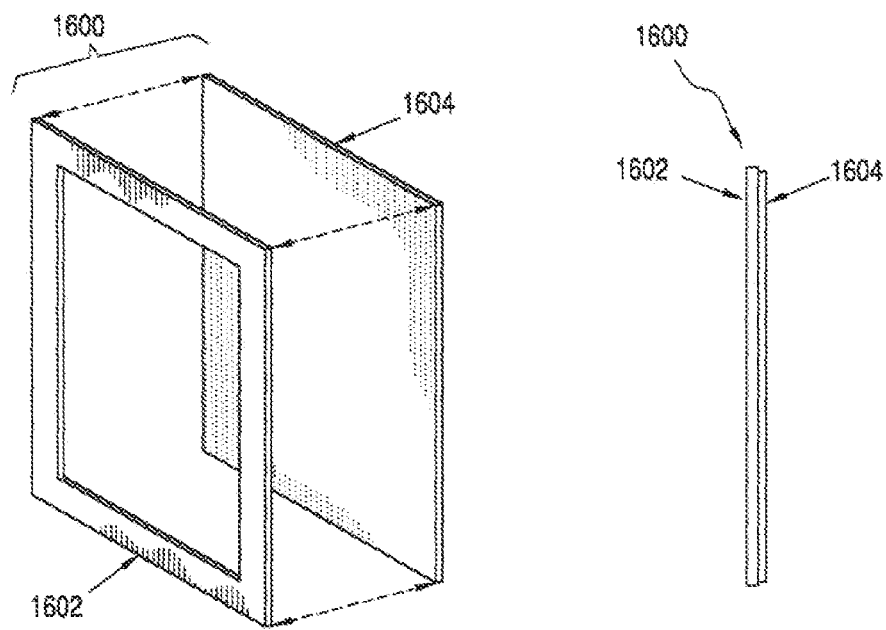
FIG. 16 is a perspective view of a filter cartridge suitable for use in practicing exemplary embodiments of this disclosure.

Shown in FIG. 16 is an exemplary filter cartridge 1600 suitable for use in practicing exemplary embodiments of this disclosure. FIG. 16 includes a separated view and a side view of filter cartridge 1600 in which the different elements have been separated. niter cartridge 1600 includes a frame 1602 and filter 1604. Frame 1602 provides a substantially rigid frame that is substantially resistant from ripping or tearing. Frame 1602 is typically made out of a cardboard or like material. Frame 1602 can be made out of any type of material that is both substantially rigid and is able to maintain its integrity during and after undergoing a sterilization cycle. Exemplary embodiments of frame 1602 can be made out of polymer based materials or cellulose based materials. In other exemplary embodiments, frame 1602 is flexible and less rigid and may become deformed or shrink during a sterilization cycle. In another exemplary embodiment, frame 1602 can be made out of any type of material that is both flexible, less rigid and is able to maintain its integrity during and after undergoing a sterilization cycle. In one exemplary embodiment, frame 1602 is composed of medical grade light board. In another exemplary embodiment, frame 1602 is composed of a silicone material. Filter 1604 can be made of any type of porous paper or cellulose type material. In other embodiments filter 1604 is made of polymeric substances, such as polypropylene. Filter 1604 is required to be porous enough to allow the passage of a sterilizing agent, such as steam through its membrane, but also resilient enough to not rip or tear during a sterilizing cycle. Exemplary embodiments of filter cartridge 1600 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1600 provide that frame 1602 and filter 1604 are removeably coupled to each other through the use of an adhesive. In another exemplary embodiment frame 1602 and filter 1604 are not removeably coupled, but are permanently affixed to one another or are integral with one another. In yet another exemplary embodiment, frame 1602 and filter 1604 are removeably coupled to each other through the use of an intermediary adhesive, such as double sided tape or the like. Exemplary adhesives are able to create a sealed interface between frame 1602 and filter 1604 and maintain the sealed interface between frame 1602 and filter 1604 prior to, during and following a sterilization cycle. One exemplary adhesive suitable for use in filter cartridge 1600 is that found is U.S. Pat. No. 3,691,140. Exemplary adhesives between frame 1602 and filter 1604 create a seal between frame 1602 and filter 1604 such that extraneous materials are not able to pass between the sealed interface of frame 1602 and filter 1604. Exemplary adhesives between frame 1602 and filter 1604 allow for filter 1604 to be removeable when desired, typically after undergoing sterilizing cycle, such that substantially all of filter 1604 can be removed in a single piece. That is, the adhesive and materials of frame 1602 and filter 1604 are selected to provide for non-destructive separation of frame 1602 and filter 1604.

Figure 17:
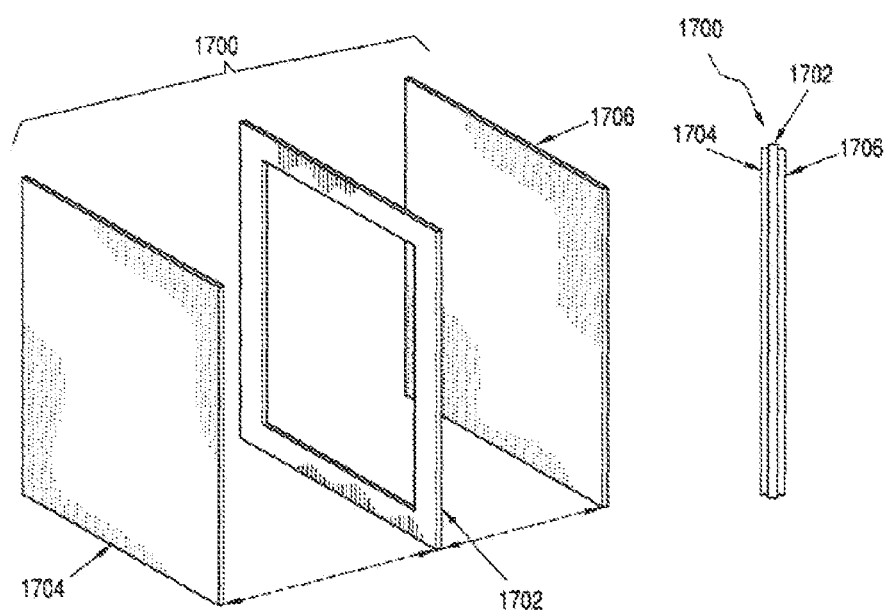
FIG. 17 is a perspective view of an alternative filter cartridge suitable in practicing exemplary embodiments of this disclosure.

Referring to FIG. 17, illustrated is filter cartridge 1700 suitable to use in practicing exemplary embodiments of this disclosure. FIG. 17 includes a separated view and a side view of filter cartridge 1700 in which the different elements nave been separated. Filter cartridge 1700 includes a frame 1702, filter 1704, and filter 1706. Frame 1702 provides a substantially rigid frame that is substantially resistant from ripping or tearing. In other exemplary embodiments, frame 1702 is flexible and less rigid and may become deformed or shrink during a sterilization cycle. Frame 1702 is typically made out of a cardboard or like material. Frame 1702 can be made out of any type of material that is both rigid and is able to maintain its integrity during and after undergoing a sterilization cycle. Exemplary embodiments of frame 1702 can be made out of polymer based materials or cellulose based materials. In another exemplary embodiment, frame 1702 can be made out of any type of material that is flexible, less rigid and is able to maintain its integrity during and after undergoing a sterilization cycle. In one exemplary embodiment, frame 1702 is composed of medical grade light board. In another exemplary embodiment, frame 1702 is composed of a silicone material.

Filter 1704 and filter 1706 can be made of any type of porous paper or cellulose type material. In other embodiments, filter 1704 and filter 1706 are made of polymeric substances, such as polypropylene. Filter 1704 and filter 1706 are required to be porous enough to allow the passage of a sterilizing agent, such as steam through its membrane, but also resilient enough to not rip or tear during a sterilizing cycle. Exemplary embodiments of filter cartridge 1700 are able to provide sufficient integrity to form a sealed interface with a confronting surface, such as a sterilizing cabinet and/or a filter door or doors, and is able to maintain its integrity during and after undergoing a sterilization cycle.

Exemplary embodiments of filter cartridge 1700 provide that frame 1702, is removeably coupled to filter 1704 and filter 1706 through the use of an adhesive. In another exemplary embodiment frame 1702, filter 1704, and filter 1706 are not removeably coupled, but are permanently affixed to one another or are integral with one another. In yet another exemplary embodiment, frame 1702 is removeably coupled to filter 1704 and filter 1706 through the use of an intermediary adhesive, such as double sided tape or the like. As shown in FIG. 17, filter 1704 and filter 1706 are removeably coupled to frame 1702 such that they are located on opposing sides of frame 1702. Exemplary adhesives are able to create a sealed interface between frame 1702 and filter 1704, and between frame 1702 and filter 1706. One exemplary adhesive suitable for use in filter cartridge 1700 is that found is U.S. Pat. No. 3,691,140. Exemplary adhesives are also able to maintain the sealed interface between frame 1702 and filter 1704 prior to, during and following a sterilization cycle, and between frame 1702 and filter 1706 prior to, during and following a sterilization cycle. Exemplary adhesives between frame 1702 and filter 1704 and between frame 1702 and filter 1706 create a seal between frame 1702 and filter 1704, and between frame 1702 and filter 1706 such that extraneous materials are not able to pass between frame 1702 and filter 1704 or between frame 1702 and filter 1706. Exemplary adhesives between frame 1702 and filter 1704, and between frame 1702 and filter 1706 allow for filter 1604 and filter 1706 to be removeable from frame 1702 when desired, typically after undergoing sterilizing cycle, such that substantially all of filter 1704 and filter 1706 can be removed in a single piece.

Figure 18:
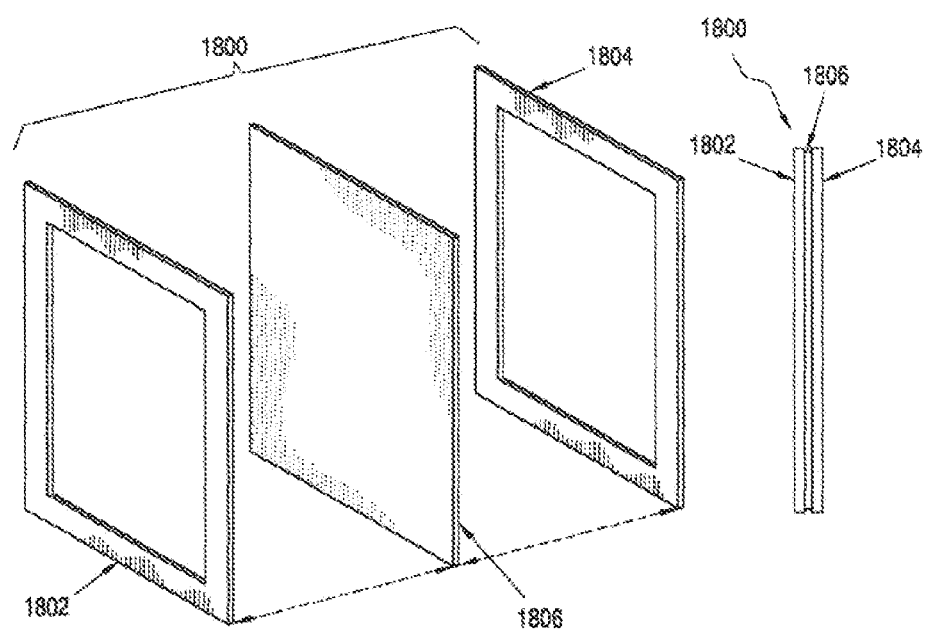
FIG. 18 is a perspective view of an alternative filter cartridge suitable in practicing exemplary embodiments of this disclosure.

Referring to FIG. 18, shown is an exemplary filter cartridge 1800 suitable for use in practicing exemplary embodiments of this disclosure. FIG. 18 includes a separated view and a side view of filter cartridge 1800 in which the different elements have been separated. Filter cartridge 1800 includes a frame 1802, frame 1804 and filter 1806. Frames 1802 and 1804 provide a substantially rigid frame that is substantially resistant from ripping or tearing. Frames 1802 and 1804 are typically made out of a cardboard or like material. Frames 1802 and 1804 can be made out of any type of material that is both substantially rigid and is able to maintain its integrity during and after undergoing a sterilization cycle. Exemplary embodiments of frames 1802 and 1804 can be made out of polymer based materials or cellulose based materials. In other exemplary embodiments, frames 1802 and 1804 are flexible and less rigid and may become deformed or shrink during a sterilization cycle. In another exemplary embodiment, frames 1802 and 1804 can be made out of any type of material that is flexible, less rigid and is able to maintain its integrity during and after undergoing a sterilization cycle. In one exemplary embodiment, frames 1802 and 1804 are composed of medical grade light board. In another exemplary embodiment, frames 1802 and 1804 are composed of a silicone material. Filter 1806 can be made of any type of porous paper or cellulose type material. In other embodiments filter 1806 is made of polymeric substances, such as polypropylene. Filter 1806 is required to be porous enough to allow the passage of a sterilizing agent, such as steam through its membrane, but also resilient enough to not rip or tear during a sterilizing cycle. Exemplary embodiments of filter cartridge 1800 are able to provide sufficient integrity to form a sealed interface with a confronting surface, such as a sterilizing cabinet and or a filter door or doors, and is able to maintain its integrity during and after undergoing a sterilization cycle.

Exemplary embodiments of filter cartridge 1800 provide that frames 1802 and 1804 are removeably coupled to filter 1806 through the use of an adhesive. In another exemplary embodiment frames 1802 and 1804, and filter 1806 are not removeably coupled, but are permanently affixed to one another or are integral with one another. In yet another exemplary embodiment, frames 1802 and 1804 are removeably coupled to filter 1806 through the use of an intermediary adhesive, such as double sided tape or the like. Exemplary adhesives are able to create a sealed interface between frame 1802 and filter 1806, and between 1804 and filter 1806 and maintain the sealed interface between frame 1802 and filter 1806, and between frame 1804 and filter 1806 prior to, during and following a sterilization cycle. One exemplary adhesive suitable for use in filter cartridge 1800 is that found is U.S. Pat. No. 3,691,140. Exemplary adhesives create a seal between frame 1802 and filter 1806, and between frame 1804 and filter 1806 such that extraneous materials do not pass between frame 1802 and filter 1806, or between frame 1804 and filter 1806. Exemplary adhesives between frame 1802 and filter 1806, and between frame 1804 and filter 1806 allow for filter 1806 to be removeable when desired, typically after undergoing sterilizing cycle, such that substantially all of filter 1806 can be removed in a single piece.

Figure 19:
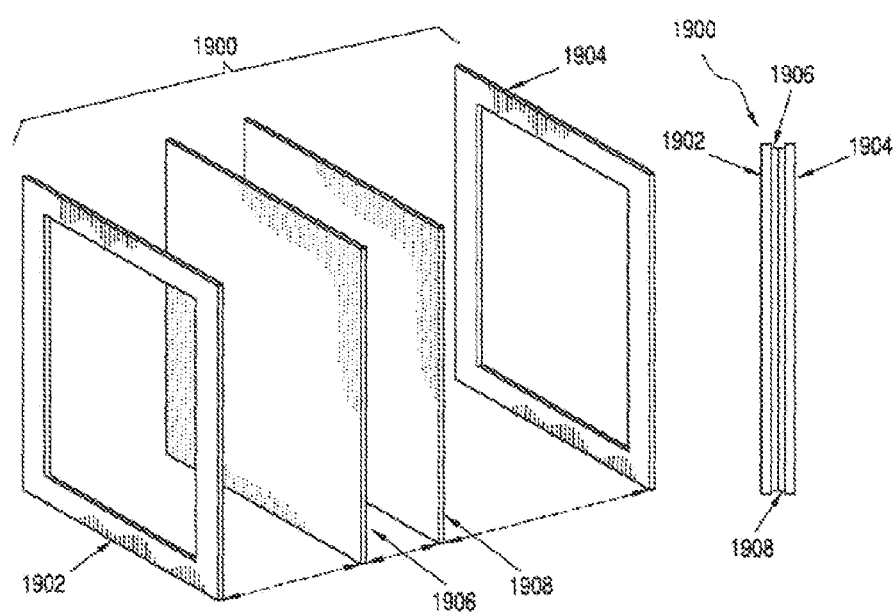
FIG. 19 is a perspective view of another filter cartridge suitable in practicing exemplary embodiments of this disclosure.

Referring to FIG. 19, shown is an exemplary filter cartridge 1900 suitable for use in practicing exemplary embodiments of this disclosure. FIG. 19 includes a separated view and a side view of filter cartridge 1900 in which the different elements have been separated. Filter cartridge 1900 includes a frame 1902, frame 1904, filter 1906 and filter 1908. Frames 1902 and 1904 provide a substantially rigid frame that is substantially resistant from ripping or tearing. Frames 1902 and 1904 are typically made out of a cardboard or like material. Frames 1902 and 1904 can be made out of any type of material that is both substantially rigid and is able to maintain its integrity during and after undergoing a sterilization cycle. In other exemplary embodiments, frames 1902 and 1904 are flexible and less rigid and may become deformed or shrink during a sterilization cycle. Exemplary embodiments of frames 1902 and 1904 can be made out of polymer based materials or cellulose based materials. In another exemplary embodiment, Frame 1902 and 1904 can be made out of any type of material that is flexible, less rigid and is able to maintain its integrity during and after undergoing a sterilization cycle. In one exemplary embodiment, frames 1902 and 1904 are composed of medical grade light board. In another exemplary embodiment, frames 1902 and 1904 are composed of a silicone material. Filters 1906 and 1908 can be made of any type of porous paper or cellulose type material. In other embodiments filters 1906 and 1908 are made of polymeric substances, such as polypropylene. Filters 1906 and 1908 are required to be porous enough to allow the passage of a sterilizing agent, such as steam through its membrane, but also resilient enough to not rip or tear during a sterilizing cycle. Exemplary embodiments of filter cartridge 1900 are able to provide sufficient integrity to form a sealed interface with a confronting surface, such as a sterilizing cabinet and or a filter door or doors, and is able to maintain its integrity during and after undergoing a sterilization cycle.

Exemplary embodiments of filter cartridge 1900 provide that frames 1902 and 1904 are removeably coupled to filters 1906 and 1908 through the use of an adhesive. In another exemplary embodiment frames 1902 and 1904, and filters 1906 and 1908 are not removeably coupled, but are permanently affixed to one another or are integral with one another. In yet another exemplary embodiment, frames 1902 and 1904 are removeably coupled to filters 1906 and 1908 through the use of an intermediary adhesive, such as double sided tape or the like. Exemplary adhesives are able to create a sealed interface between frame 1902 and filter 1906, between frame 1904 and filter 1906, between frame 1904 and filter 1908 and also maintain the sealed interface between frames 1902 and 1904, and filters 1906 and 1908 prior to, during and following a sterilization cycle. One exemplary adhesive suitable for use in filter cartridge 1900 is that found is U.S. Pat. No. 3,691,140. Exemplary adhesives between frames 1902 and 1904, and filters 1906 and 1908 create a seal between frames 1902 and 1904, and filter 1906 and 1908 such that extraneous materials do not pass between frames 1902 and 1904, and filters 1906 and 1908. Exemplary adhesives between frames 1902 and 1904, and filters 1906 and 1908 allow for filters 1906 and 1908 to be removeable from frames 1902 and 1904 when desired, typically after undergoing sterilizing cycle, such that substantially all of filters 1906 or 1908 can be removed in a single piece.

In another exemplary embodiment, as shown in FIGS. 20-25, the sterilization cabinet 2202, 2502, 2602, is a rigid container having an enclosing wall such as a plurality of walls and a door 2002, 2100, 2204, 2304, 2512, and 2612 defining an interior volume. The sterilization cabinet 2202, 2502, 2602, further includes at least one wall or door defining a venting pass through area 140. A filter 2510, 2306, 1302, 1402, 1502, 1602, and 1700 may occlude the venting pass through area 140. The sterilization cabinet 2202, 2502, and 2602 is constructed of 304 stainless steel with an anodized aluminum filter housing/door. The sterilization container 2202, 2502, 2602, however, can be constructed of other types of stainless steel, or other types of materials as well.

The sterilization cabinet 2202, 2502, 2602 may have a fenestrated door 2506, 2612 holding a filter 2510, 2306, 1302, 1402,1502, 1602, 1700. In one configuration, the filter 2510, 2306, 1302, 1402, 1502, 1602, 1700 is a single-use filter. The sterilization cabinet 2202 2502, 2602 is designed to be used in a steam autoclave and may hold multiple open trays containing surgical instruments. Trays within the container 2202, 2502, 2602 may be separated by spacers 902 having dividers or lips 904 along the edges of spacer 902 and throughout the midsection of spacer 902 to ensure separation and maximum steam exposure. The sterilization cabinet 2202, 2502, and 2602 has been validated to sterilize 375 lbs. of instruments along with the spacers 902. The validation was conducted with 15 instrument trays at 25 lbs. Actual expected loads in hospital settings are likely to be less. For example, loads in a hospital setting are more typically 140 lbs or less, and even more typically approximately 110 lbs. It should be appreciated that sterilized instruments can be stored for up to 30 days within the closed (intact filters) sterilization container.

The sterilization cabinet 2202, 2502, 2602 is loaded into the sterilizer, for example, an autoclave, with a transfer carriage (not shown).

The use of a single-use disposable filter cartridge 1302, 1402, 1502, 1602, 1700 installed in the fenestrated door 2506, 2612 eliminates the need for a sealed gasket found on prior systems. The omission of a reusable gasket eliminates contamination risks due to failed reusable gaskets. It is understood the single use disposable filter can be used with a separate or integral cartridge.

The sterilization cabinet 2202, 2502, 2602 is indicated for enclosing other medical devices that are to be sterilized by a healthcare provider. It is intended to allow sterilization of the enclosed materials and maintain sterility for up to 30 days until used. The sterilization cabinet 2202, 2502, 2602 is intended to be used in pre-vacuum steam sterilizers with a prevacuum cycle of 270° F. (132° C.) and exposure time of 4 minutes. The sterilization cabinet 2202, 2502, 2602 is intended to be used with Turbett Surgical filters.

Validation was done using three trays per level and a maximum instrument load of 25 lbs. per tray. The validation load included six 1 mm×500 mm lumens and six 3 mm×400 mm lumens. The total weight of instruments and trays validated is 375 lbs. The trays holding instruments within the sterilizing cabinet 100 were uncovered, perforated or wire mesh general delivery trays.

The principal material of construction of the sterilization cabinet 2202, 2502, 2602 may be stainless steel and aluminum. However, it should be appreciated that other materials may be used. In one configuration, the overall size is 34"×24"×22". The empty container 210 weighs approximately 136 lbs. It is thus a relatively large container, typically associated with a transfer cart. In this configuration, the venting pass through area includes 905 holes, each having a diameter of approximately 0.74 inches, thus providing a venting pass through area of 398.2 (approximately 400) square inches. Thus, in an exemplary embodiment, the where the volume is approximately 17,952, cubic inches based on the overall size, the venting pass through area to volume ratio is approximately 0.022 inch$^2$ per inch$^3$ or 11 square inches:500 cubic inches. If internal dimensions provide a volume of approximately 14,846 cubic inches, the venting pass through area to volume ratio is approximately 0.027 inch$^2$ per inch$^3$ or 27 square inches:1000 cubic inches. It should be appreciated that exemplary embodiments of the sterilization cabinet can be other dimensions, shapes and sizes that provide similar vent to volume ratios, wherein the ratio is at least approximately 0.022 inch$^2$ per inch$^3$ or 11 square inches:500 cubic inches, and in select configurations between 0.008-0.21 inch$^2$ per inch$^3$, (1 square inch:125 cubic inches and 21 square inches:100 cubic inches) and in further configurations, between 0.16-0.2 inch$^2$ per inch$^3$ (4 square inches:25 cubic inches and 1 square inch:5 cubic inches). That is, the sterilization container, such as the cabinet may be configured of any shape or size so long as the venting pass through area has dimensions corresponding to the volume to provide the desired vent area to volume ratio. Similarly, the venting area may have many shapes, sizes and/or locations on the sterilization cabinet, so long as the venting area and volume meet the vent pass through area to volume ratios.

Figure 20:
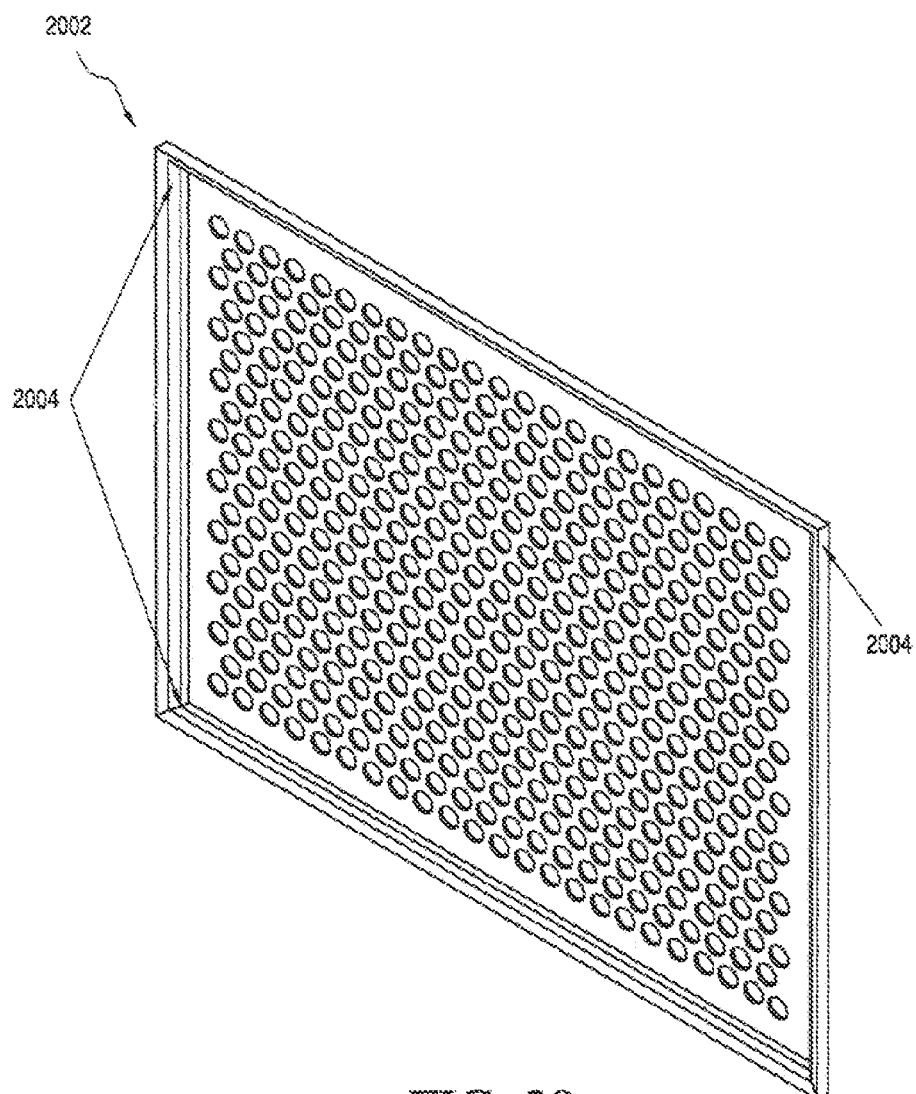
FIG. 20 is a filter cartridge holder suitable in practicing exemplary embodiments of this disclosure.

Referring to FIG. 20, shown is an exemplary filter door for a filter cartridge suitable for use in practicing exemplary embodiments of this disclosure. Shown in FIG. 20 is an exemplary outer filter door 2002. Filter door 2002 includes tabs or catches 2004, which protrude perpendicular from the back face of filter door 2002. Filter door 2002 as illustrated in FIG. 20 contains numerous holes or openings along its surface, which allow for the passage of sterilizing steam. In the embodiment depicted in FIG. 20, the tabs or catches 2004 are located in each of the four corners of filter door 2002. However, it should be noted that in other exemplary embodiments there can be more or less than four tabs or catches 2004. Additionally, tabs or catches 2004 can be located in different arrangements. Exemplary tabs or catches 2004 provide a mechanism for removeably locating or placing a filter cartridge on filter door 2002, such that a filter cartridge can be placed between tabs or catches 2004 and is in contact with tabs or catches 2004 without bending, folding or otherwise compromising the integrity of a filter cartridge.

Figure 21:
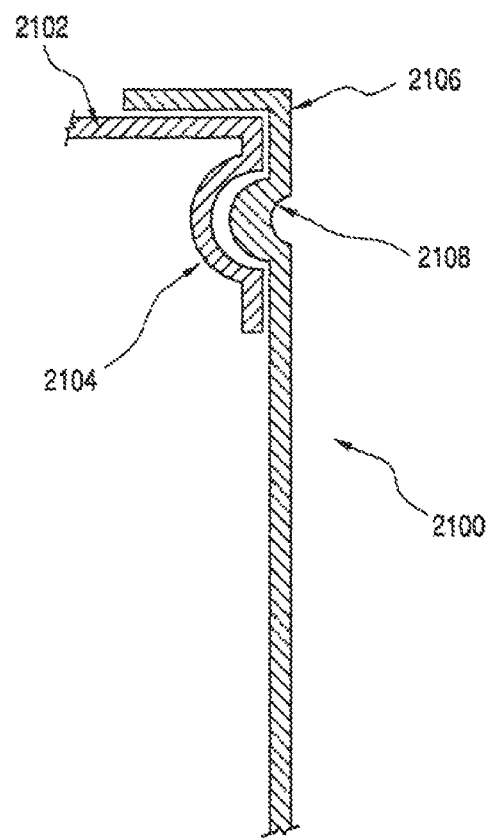
FIG. 21 is a magnified cross-sectional view of a sterilization container such as a sterilization cabinet and a filter door suitable for use in practicing exemplary embodiments of this disclosure.

Referring to FIG. 21, shown is a magnified cross-sectional view of an exemplary sterilizing cabinet and filter door suitable for use in practicing exemplary embodiments of this disclosure. Shown in FIG. 21 is a cross-sectional view of sterilizing cabinet 2102 with trough section 2104, and filter door 2106 with trough section 2108. Exemplary embodiments of trough section 2104 and trough section 2106 run along the entire edge of sterilizing cabinet 2102 and filter door 2106. Trough section 2104 and trough section 2106 are shaped such that a sealed interface is maintained throughout the trough (i.e., between trough section 2104 and trough section 2106) when a single filter, multiple filters, or a filter cartridge is placed between trough section 2104 and trough section 2106. Exemplary embodiments of trough section 2104 and trough section 2106 have a size and depth such that the movement of extraneous materials through the sealed interface between sterilizing cabinet 2102 and filter door 2106 is substantially prevented. In practice, a filter cartridge may be placed and compressed between the sterilizing cabinet 2102 and filter door 2106 such that the filter cartridge is deformed into the shape of the trough in which it is compressed.

Figure 22:
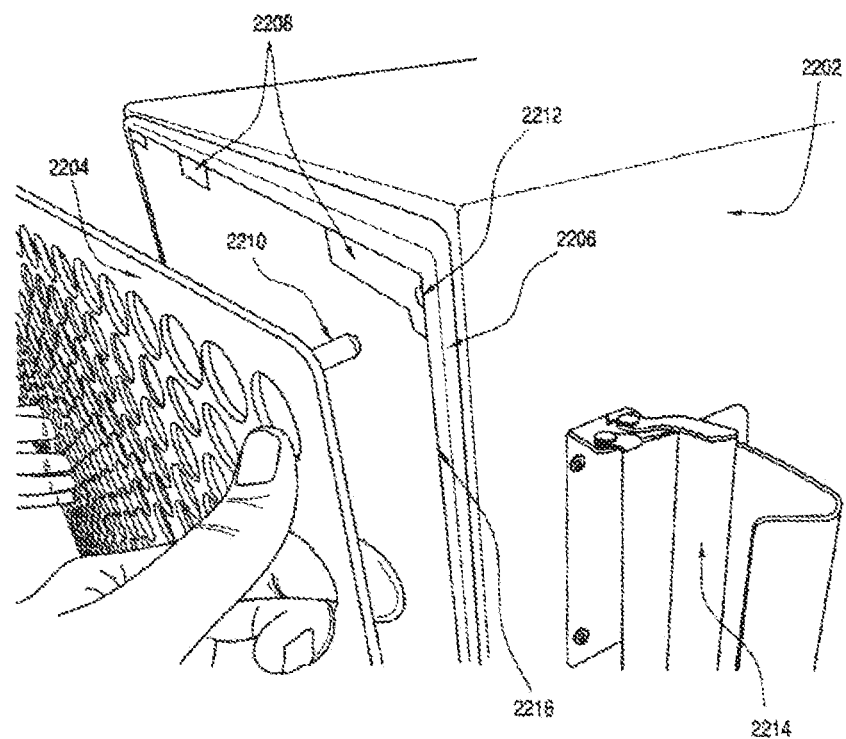
FIG. 22 is a perspective view of an exemplary a sterilization container such as a sterilization cabinet and filter door suitable for use in practicing exemplary embodiments of the present disclosure.

Referring to FIG. 22, shown is a perspective view of an exemplary sterilizing cabinet and filter door suitable for use in practicing exemplary embodiments of the present disclosure. Illustrated in FIG. 22 is sterilizing cabinet 2202, filter door 2204, trough section 2206, sterilizing cabinet tab 2208, filter door pin 2210, pin hole 2212, and clamp 2214. Exemplary embodiments of filter door pin 2210 are located on the top two corners of filter door 2204. In other exemplary embodiments, filter door pins 2210 are located at all four corners of filter door 2204. Filter door pins 2210 are of the size and shape to fit within pin hole 2212. Exemplary embodiments of filter door pin 2210 and pin hole 2212 are located such that filter door 2204 properly aligns and covers the open front of sterilizing cabinet 2202. Exemplary embodiments of filter door pin 2210 and pin hole 2212 maintain filter door 2204 is a loosely attached position to sterilizing cabinet 2202.

In other exemplary embodiments, filter door 2204 with filter door pin 2210 aligns with pin holes 2212 on sterilizing cabinet 2202 such that there is a small gap between the edge 2216 of sterilizing cabinet 2202 and filter door 2204. It can be appreciated that pin hole 2212 is located on sterilizing cabinet tab 2208. Exemplary embodiments of sterilizing cabinet tab 2208 are located at least in the four corners of sterilizing cabinet 2202 along edge 2216. In other exemplary embodiments, a sterilizing cabinet tab 2208 is also located within the middle of the vertical and horizontal edge 2216 of sterilizing cabinet 2202 such that there are eight (8) sterilizing cabinet tabs 2208. In another exemplary embodiment sterilizing cabinet 2202 includes one or more sterilizing cabinet tab 2208. Exemplary embodiments of sterilizing cabinet tab 2208 overlap with filter door 2204 when placed over the front opening of sterilizing cabinet 2202 such that filter door 2204 is prevented from falling or moving into the interior of sterilizing cabinet 2202 when filter door 2204 is aligned with pin hole 2212.

FIG. 22 also shows clamp 2214. Exemplary embodiments of clamp 2214 are located on the vertical sides of sterilizing cabinet 2202. However, exemplary embodiments of clamp 2214 can be placed in many different arrangements along the sides of sterilizing cabinet 2202 such that clamps 2214 are able to clasp and maintain filter door 2204 in a sealed position over the open front of sterilizing cabinet 2202. Exemplary embodiments of clamps 2214 are able to clasp and release filter door 2204 and an outer filter door from sterilizing cabinet 2202. Exemplary embodiments of clamp 2214 are sized such that a sealed interface is created between sterilizing cabinet 2202, a filter or filters, and the filter doors. The sealed interface prevents the passage of extraneous materials between the filter doors and sterilizing cabinet 2202.

Figure 23:
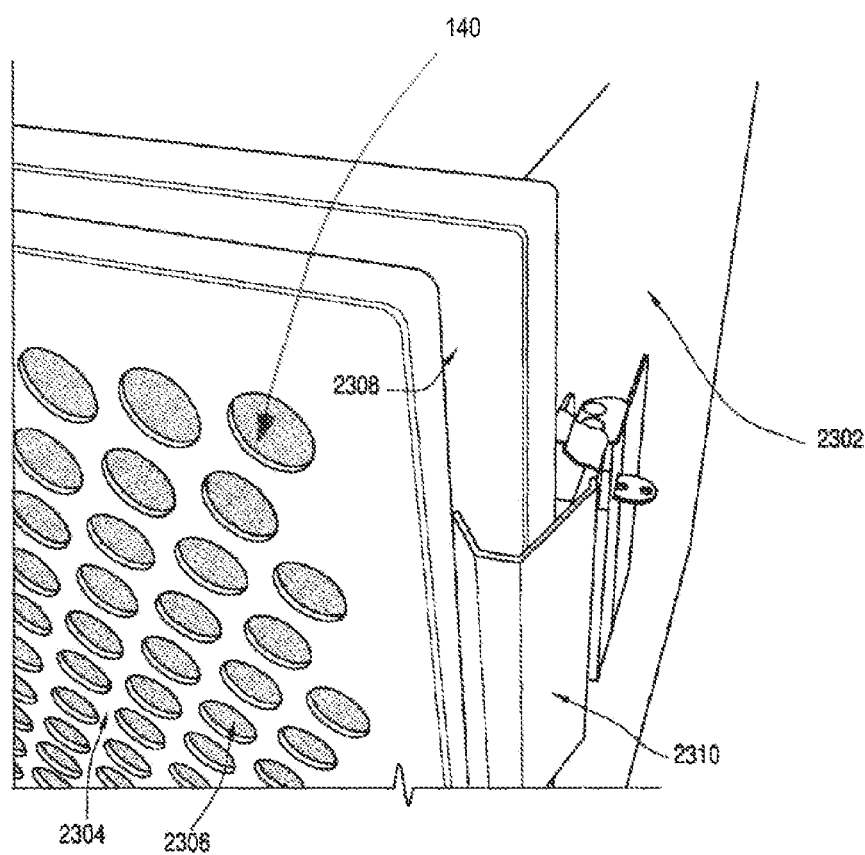
FIG. 23 is a perspective view of an exemplary a sterilization container such as a sterilization cabinet and filter door suitable for use in practicing exemplary embodiments of the present disclosure.

With reference to FIG. 23, shown is a perspective view of an exemplary sterilizing cabinet and filter door suitable for use in practicing exemplary embodiments of the present disclosure. Shown in FIG. 23 are sterilizing cabinet 2302, filter door 2304, filter cartridge 2306, clamp trough 2308, and clamp 2310. As illustrated, filter door 2304 includes clamp trough 2308 around the outer edge of filter door 2304. Exemplary embodiments of clamp trough 2308 align with the trough section of sterilizing cabinet 2302 when filter door 2304 covers the opening of sterilizing cabinet 2302.

Additionally, clamp trough 2308 is sized and located such that clamp 2310 is able to latch, clamp or otherwise hook onto filter door 2304 through clamp trough 2308. Exemplary embodiments of clamp trough 2308 provides a lip or trough that substantially prevents clamp 2310 from slipping when clamp 2310 clamps onto filter door 2304.

Figure 24:
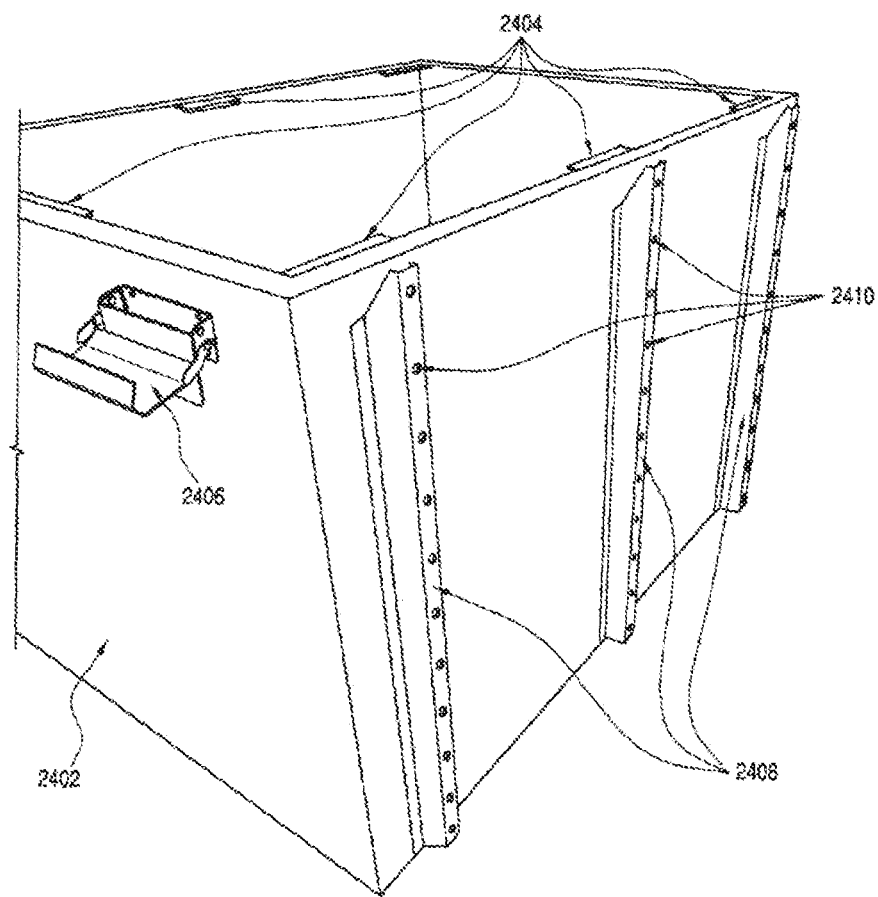
FIG. 24 is a bottom perspective view of an exemplary sterilization container such as a sterilization cabinet suitable for use in practicing exemplary embodiments of the present disclosure.

Referring to FIG. 24, shown is a bottom perspective view of an exemplary sterilizing cabinet suitable for use in practicing exemplary embodiments of the present disclosure. Shown in FIG. 24 are sterilizing cabinet 2402, sterilizing cabinet tabs 2404, clamp 2406 and legs 2408. Exemplary embodiments of legs 2408 reside on the bottom of sterilizing cabinet 2402 and provide a stable foundation for sterilizing cabinet 2402 to rest on a surface. Exemplary embodiments of legs 2408 further include holes 2410. Holes 2410 provide a means for attaching legs 2408 and thus sterilizing cabinet 2402 to a surface. For example, sterilizing cabinet 2402 through holes 2410 on legs 2408 can be screwed, bolted, attached, or nailed onto a table, counter, or other flat surface large and structurally sturdy enough to maintain sterilizing cabinet 2402.

Figure 25:
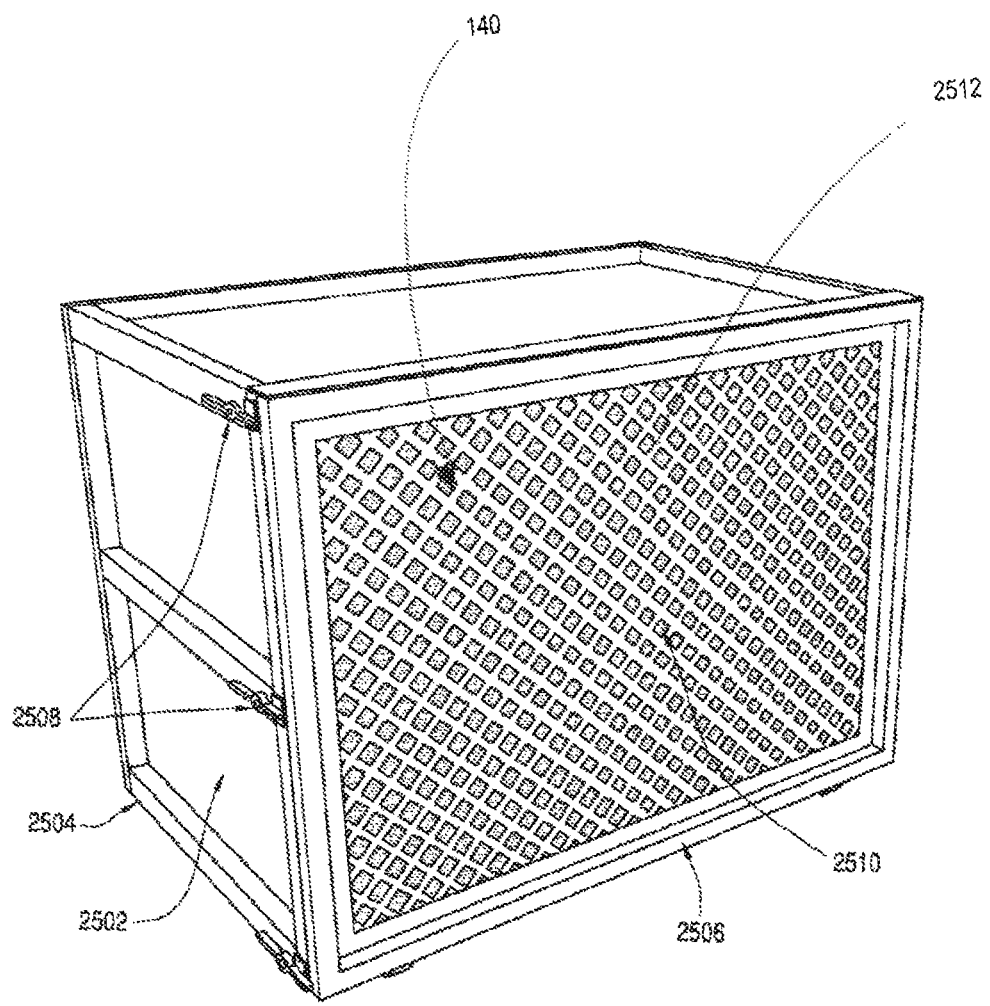
FIG. 25 is a perspective view of an alternative embodiment of a sterilization container such as a sterilization cabinet suitable for use in practicing exemplary embodiments of this disclosure.

Referring to FIG. 25, shown is a perspective view or an alternative embodiment of a sterilizing cabinet suitable for use in practicing exemplary embodiments of this disclosure. Shown in FIG. 25 are sterilizing cabinet 2502, frame 2504, filter door 2506, latches 2508, and filter 2510. As illustrated, sterilizing cabinet 2502 is maintained within frame 2504. Frame 2504 provides a structurally reinforcing frame for sterilizing cabinet 2502. Exemplary embodiments of frame 2504 are able to securely maintain sterilizing cabinet 2502 such that all of the sides/corners of sterilizing cabinet 2502 are supported by frame 2504. Exemplary embodiments of frame 2504 are made of any type of metal, plastic, composite, or aluminum alloy. Exemplary embodiments of frame 2504 are able to repeatedly undergo sterilizing cycles (e.g., steam sterilizing cycles) and maintain its structural integrity.

Filter door 2506 attaches to frame 2504 through the use of latches 2508. However, it should be appreciated that latches 2508 can include any type of clamping, latching or clasping device known in the art that is able to releasable attach filter door 2506 to frame 2504 such that a sealed interface is created between filter door 2506 and sterilizing cabinet 2502.

Figure 26:
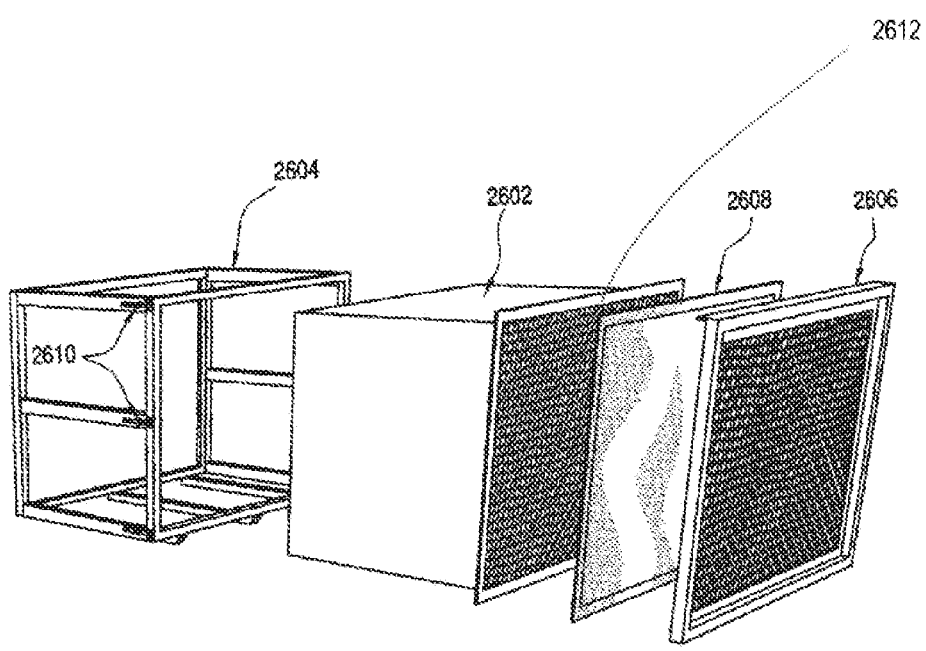
FIG. 26 is a perspective view of a separated alternative embodiment of a sterilization container such as a sterilization cabinet suitable for use in practicing exemplary embodiments of this disclosure.

Referring to FIG. 26, shown is a perspective view of a separated alternative embodiment of a sterilizing cabinet suitable for use in practicing exemplary embodiments of this disclosure. Shown in FIG. 26 are sterilizing cabinet 2602, frame 2604, filter door 2606, filter cartridge 2608, and latches 2610. In some embodiments, as shown in FIG. 26, sterilizing cabinet 2602 can be removed from frame 2604 when filter door 2606 is released from removable frame 2604 by latches 2610. In other exemplary embodiments, frame 2604 is not removable from sterilizing cabinet 2602, but is fixedly attached to sterilizing cabinet 2602. Filter door 2606 as depicted includes a fenestrated grid throughout its center. However, exemplary embodiments of filter door 2606 include any type of arrangement of holes, gaps, or grids such that sterilizing steam is free to pass through the center portion of filter door 2606.

During a sterilizing cycle filter cartridge 2608 is maintained between filter door 2606 and sterilizing cabinet 2602. As previously stated above, filter cartridge 2608 is placed between filter door 2606 and sterilizing cabinet 2602 creating a sealed interface around its edges such that sterilizing steam is not able to pass between the sealed interface, but can only pass through the center of filter cartridge 2608.

Technological Characteristics:

The sterilization cabinet 2202, 2502, 2602 has been validated to sterilize 375 lbs. of instruments along with the spacers 902. The validation was conducted with 15 instrument trays at 25 lbs. each to represent the most challenging case. The validations included thermal profile, sterilization efficacy, and drying in a pre-vacuum steam sterilizer. Sterilized instruments can be stored for up to 30 days within the closed container.

The sterilization cabinet 2202, 2502, 2602 is constructed of 304 stainless steel sheet metal on a rigid stainless steel frame. The sterilization container, such as the cabinet opens from the side for easy placement and retrieval of surgical trays. In one configuration, a sidewall is omitted to define a door way or opening to the cabinet for inserting and removing trays (medical instruments). A filter 1700 comprised of 1 or 2 layers of filter paper 1704, 1706 and a compressible gasket 1702 is placed between the door and the cabinet, such that a portion of the filter or gasket is disposed between the door and the cabinet to form a sealed interface. After use (the sterilization process and removal of the trays (the sterilized medical instruments), the filter 1700 having the compressible gasket 1702 is discarded.

The following testing was conducted to establish substantial equivalence and efficacy:
ANSI/AAMI ST77: Containment Devices for Reusable Medical Device Sterilization testing:
Pre-vacuum thermal profile
Steam pre-vacuum sterilization efficacy
Pre-vacuum dry time
Microbial aerosol challenge
30 day shelf-life study
AAMI TIR 30: A Compendium of Processes, Materials, Test Methods and Acceptance Criteria for Cleaning Reusable Medical Devices testing:
Protein analysis and Total Organic Carbon Manual cleaning methods
ANSI/AAMI HE75: Human Factors Engineering—Design of Medical Devices testing:
Human factors usability study Turning now to FIG. 25, the sterilization cabinet 2202 includes door 2204 having a large vented area 2512. In one configuration, the venting pass through area of the door 2204 includes a plurality of holes or a fenestrated grid throughout its center. For example, the venting pass through area 2512 of the door 2204 includes approximately 461 holes, each having an area of approximately 0.82 square inches, thus providing a venting pass through area 2512 of 377 inch$^2$. The sterilization cabinet 2202 having an interior volume of approximately 17,952 inch$^3$ would thus, have a venting pass through area of 377 inch$^2$ compared to a volume of 17,952 inches$^3$, or a ratio of approximately 0.021 inch$^2$ per inch$^3$ or 21 square inches:1000 cubic inches.

Exemplary embodiments of sterilization cabinet 2202 can include a single vent or a plurality of vents to define the venting pass through area, so long as the venting pass through area to volume ratio between 0.008-0.21 inch$^2$ per inch$^3$ (or 1 square inch:125 cubic inches and 21 square inches:1000 cubic inches) and in select configurations between 0.16-0.21 inch$^2$ per inch$^3$ (or 4 square inches:25 cubic inches and 21 square inches:1000 cubic inches), or in further configurations equal to or greater than 0.021 inch$^2$ per inch$^3$ or 21 square inches:1000 cubic inches.

The high venting pass through area to volume ratio reduces the drying time required after the sterilization cycle. That is, assuming multiple trays of medical instruments in a sterilization cabinet 100, for example, up to 15 trays, are placed in a sterilizer device, such as an autoclave, the sterilization cabinet 2202, with the venting pass through area to volume ratio of 0.021 per inch, would require a dry time of less than 30 minutes, and more specifically approximately 10-15 minutes, and even more specifically, 10 minutes. In one configuration, a dry time of less than 15 minutes is provided when a ratio of the venting pass through area to the interior volume of the sterilization cabinet 2202 is between 0.008-0.21 inch$^2$ per inch$^3$ (or 1 square inch:125 cubic inches and 21 square inches:1000 cubic inches). In another configuration, the drying time is approximately 10 minutes for up to 140 lbs of medical instruments arranged in the sterilization cabinet 2202 on multiple trays.

In one configuration, the sterilization container has dimensions of approximately 34 inch by 22 inch by 24 inch and the door has 869 holes at 0.766" diameter and 32 holes at 0.5" diameter. Thus, the vented pass through area is 400 inch$^2$ plus approximately 6 inch$^2$. Thus, the ratio of the venting pass through area to the interior volume of the sterilization cabinet is approximately 406 inch$^2$ to 17952 inch$^3$ or 0.0226 inch$^2$ per inch$^3$.

Figure 27:
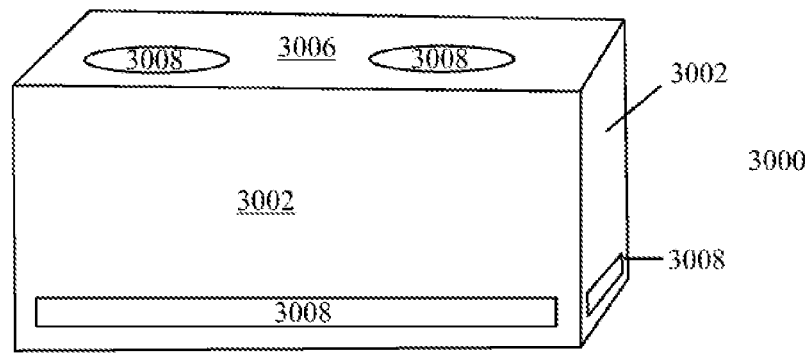
FIG. 27 is a perspective view of an alternative embodiment of a sterilization container such as a sterilization cabinet suitable for use in practicing exemplary embodiments of this disclosure.
Figure 28:
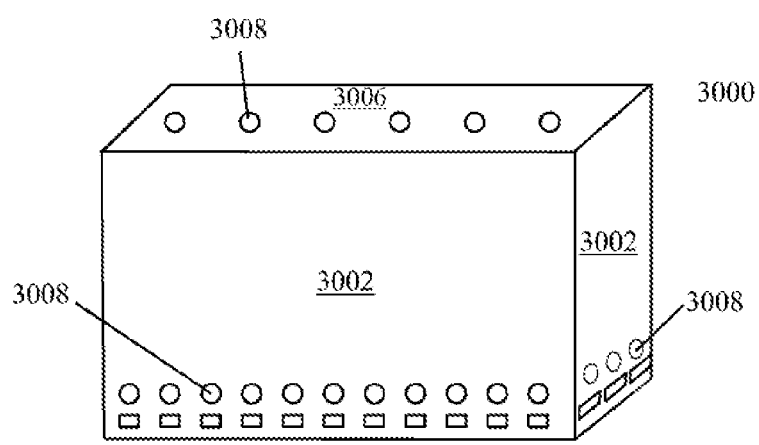
FIG. 28 is a perspective view of yet another alternative embodiment of a sterilization container such as a sterilization cabinet suitable for use in practicing exemplary embodiments of this disclosure.

As shown in FIGS. 27 and 28, the sterilization cabinet 3000 includes a plurality of sidewalls 3002 and a door (not shown). The sterilization cabinet 3000 can hold multiple trays for holding medical instruments. In one configuration, the sterilizing cabinet 3000 can hold up to 15 trays. At least one of the sidewalls 3002 includes a large vented area. For example, as shown in FIGS. 27 and 28, walls 3002 include a vented portion 3008 along the lower portion of the walls and a vented portion along top walls 3006. The vented portion 3008 may include a large vent, or multiple vents of any shape and size that provide the venting pass through area to volume ratio. In one configuration, the vented portion 3008 includes rectangular vents along a lower portion of the sidewalls 3002 and smaller oval or circular vents along top wall 2006. It should be appreciated that the vents 2008 along the lower portion of walls 3002 may permit drainage of condensate to further decrease the amount of dry time required during the sterilization process.

In one configuration, the total venting pass through area 3008 of the sidewalls 3002 and top wall 3006 to the interior volume of the sterilization cabinet 3000 ratio is greater than 0.008 inch$^2$ per inch$^3$. The high venting pass through area to volume ratio is sufficient to provide a dry time of 30 minutes or less, and more preferably 15 minutes, and even more preferably 10 minutes. In one configuration, these drying times are achieved when 140 lbs of medical instruments are loaded on trays in the sterilization cabinet 3000. The venting pass through areas 3008 of the sterilization cabinet 3000 may be smaller or larger, of a different shape, or provided on a different location of the sidewalls, top wall, bottom wall, and/or door, or include a plurality of holes or a fenestrated grid throughout its center, provided, however, that the venting pass through area to volume ratio is greater than 0.008 inch$^2$ per inch$^3$ (or 1 square inch:125 cubic inches).

Figure 29:
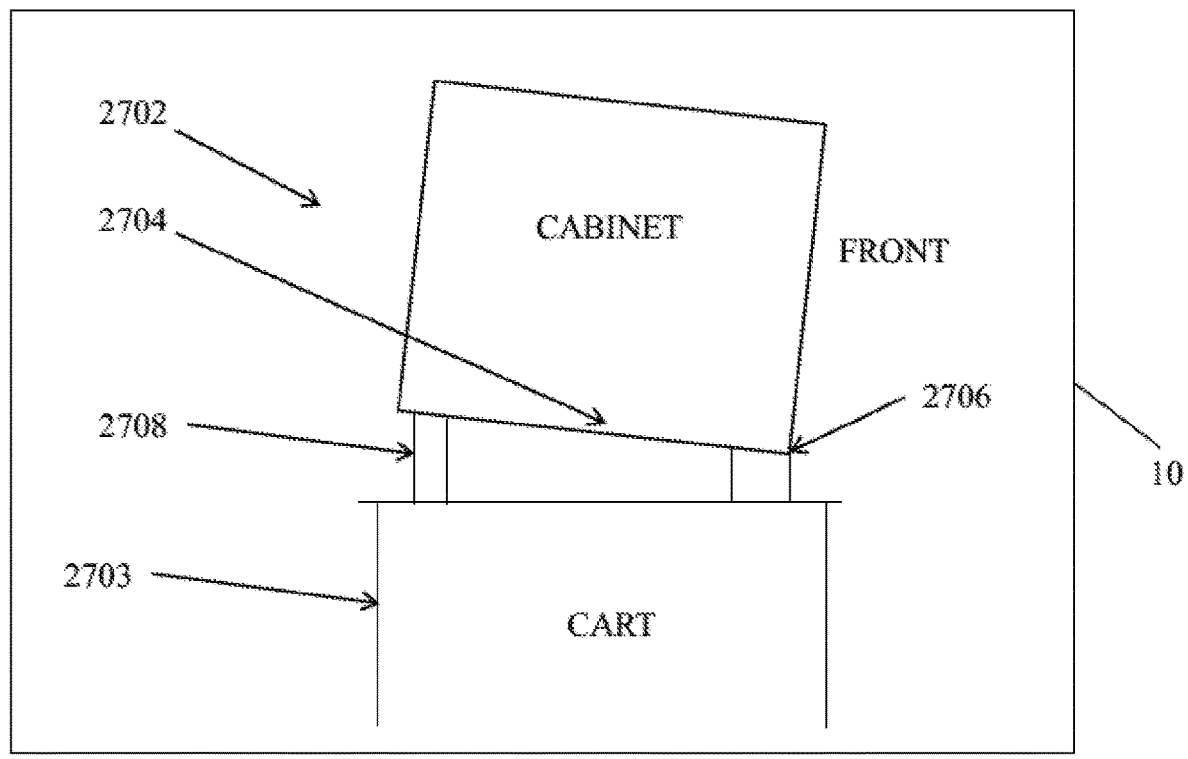
FIG. 29 is a side view of an embodiment of a sterilizing cabinet suitable for use in practicing exemplary embodiments of this disclosure.

Referring to FIG. 29, illustrated is a side view of an embodiment of a sterilizing cabinet in an autoclave 10. Shown in FIG. 29 is a sterilizing cabinet 2702 with bottom 2704, front legs 2706, and back legs 2708. Front legs 2706 and back legs 2708 as shown in FIG. 29 are pegs or stands fixedly attached to bottom 2704 of sterilizing cabinet 2702, which provide support for sterilizing cabinet 2702 when placed on a substantially planar surface. As shown in FIG. 29, there are two front legs 2706 and two back legs 2708. However, it should be appreciated that exemplary embodiments of front legs 2706 and back legs 2708 can include one or more than one leg or support provided that front legs 2706 are shorter than back legs 2708 which in turn tilts or angles bottom 2704 toward the front of sterilizing cabinet 2702. In other words, front legs 2706 and back legs 2708 include any arrangement resulting in bottom 2704 not being a level surface but tilted, inclined, towards a vent port of sterilizing cabinet 2702. Preferably, the bottom 2704 is sufficiently inclined to induce a flow of condensate to and through the vent port.

In another exemplary embodiment, sterilizing cabinet 2702 includes a single front leg 2706 that spans or substantially spans the front width of sterilizing cabinet 2702, and a single back leg 2708 that spans or substantially spans the back width of sterilizing cabinet 2702. in yet another embodiment, sterilizing cabinet 2702 includes two front legs 2706 located in opposite front corners of bottom 2704 of sterilizing cabinet 2702, and a single back leg 2708 located in the middle or substantially the middle of the back of bottom 2704 of sterilizing cabinet 2702.

In a further exemplary embodiment, front legs 2706 and back legs 2708 are adjustable such that their length or height can be manually changed. It is contemplated that sterilizing cabinet 2702 can include actuators, such as servos, pistons, or lifts that can be remotely engaged to tilt the bottom 2704 to selectively induce flow along the bottom to the vent port.

Exemplary embodiments of bottom 2704 provide a flat surface that when tilted, towards the front of sterilizing cabinet 2702 which contains a vent port and a filter, allows a liquid, such as condensate to flow along bottom 2704 to and through the filter and out of sterilizing cabinet 2702. In practice, when sterilizing cabinet 2702 undergoes a sterilization cycle, sterilizing cabinet 2702 is placed in an autoclave or other known sterilizing device. The autoclave is then shut and sterilizing steam passes through a filter or filters overlaying a front vent port to the interior of sterilizing cabinet 2702 at which point the sterilizing steam comes into contact with any items or materials within the interior of sterilizing cabinet 2702. This process can produce a substantial amount of condensate within the interior of sterilizing cabinet 2702, which can collect on the bottom 2704 of sterilizing cabinet 2702. For example, approximately 12 ounces of condensate may be produced for every 15 pounds of load maintained within sterilizing cabinet 2702 during a sterilization cycle of the autoclave. Exemplary embodiments of bottom 2704 provide a surface that allows the condensate to flow or move freely towards a filter on sterilizing cabinet 2702, such as the front of the cabinet, so that the condensate can exit the interior of sterilizing cabinet 2702. Exemplary embodiments of the sterilizing cabinet 2702 further provide for at least a substantial portion, and in select configurations all of the condensate within sterilizing cabinet 2702 to have exited sterilizing cabinet 2702 prior to the opening of the autoclave 10 or other sterilizing device. In yet another exemplary embodiment, sterilizing cabinet 2702 contains an industry acceptable amount of condensate following a sterilizing cycle, when the autoclave is opened.

Exemplary embodiments of bottom 2704 also include surfaces that are not substantially flat, but have channels, features or minor curves that move or allow to move condensate or accumulated condensate to a vent port of sterilizing cabinet 2702 through a filter or to another predetermined outlet or filtered drain that exits the interior of sterilizing cabinet 2702.

Figure 30:
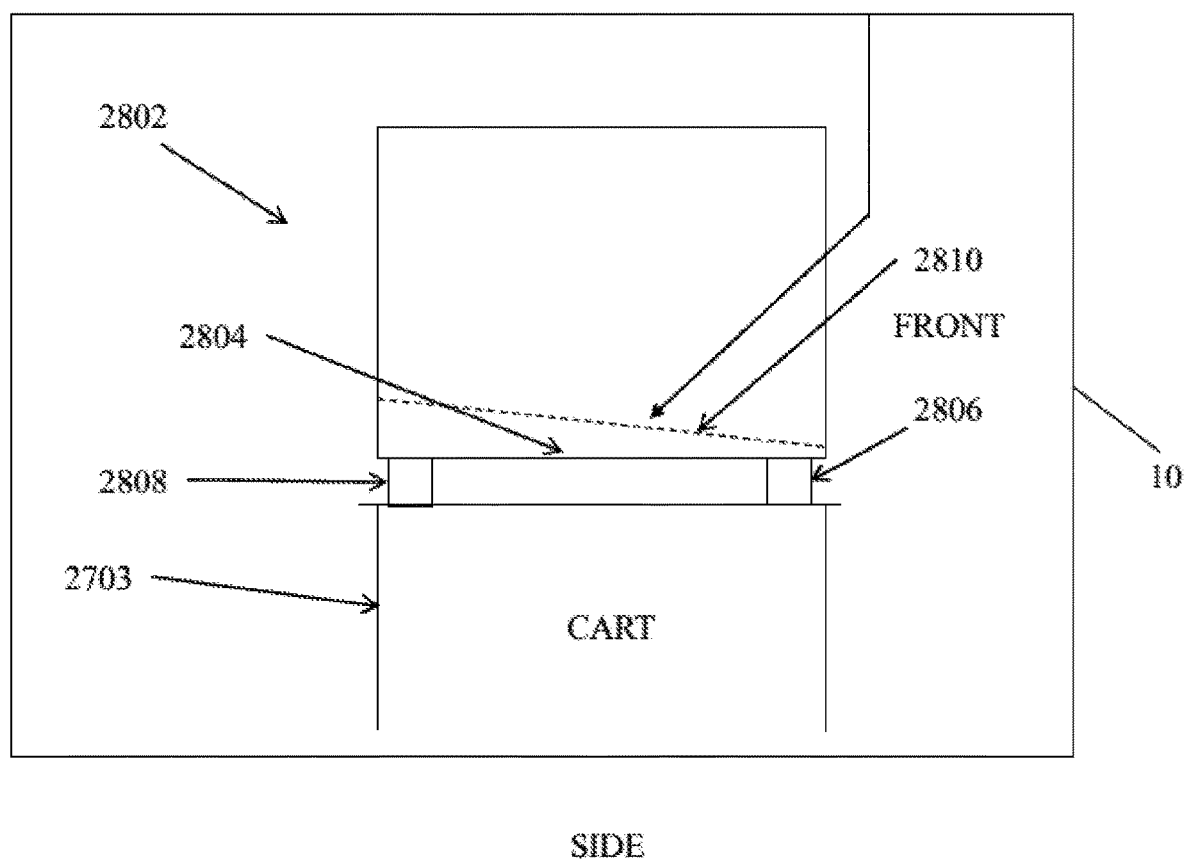
FIG. 30 is another embodiment of a sterilizing cabinet suitable for use in practicing exemplary embodiments of this disclosure.

Shown in FIG. 30 is sterilizing cabinet 2802, bottom 2804, front legs 2806, back legs 2808, and raised floor 2810 within the autoclave 10. In this embodiment, front legs 2806 and back legs 2808 are the same length or height such that bottom 2804 as well as sterilizing cabinet 2802 is level when placed on a level planar surface. Raised floor 2810 as depicted is located above bottom 2804 in the interior or sterilizing cabinet 2802.

Raised floor 2810 in one embodiment is substantially planar. Exemplary embodiments of raised floor 2810 provide a surface that allows or moves a flow of condensate toward a vent port located on the front of sterilizing cabinet 2802 and through the filter overlying the vent port. In another exemplary embodiment, raised floor 2810 is a surface that is not substantially planar, but is curved or has minor curves, or flow channels that moves or allows to move a flow of condensate or accumulated condensate to a vent port of sterilizing cabinet 2802 or to another predetermined outlet or filtered drain that exits the interior of sterilizing cabinet 2802.

Figure 31:
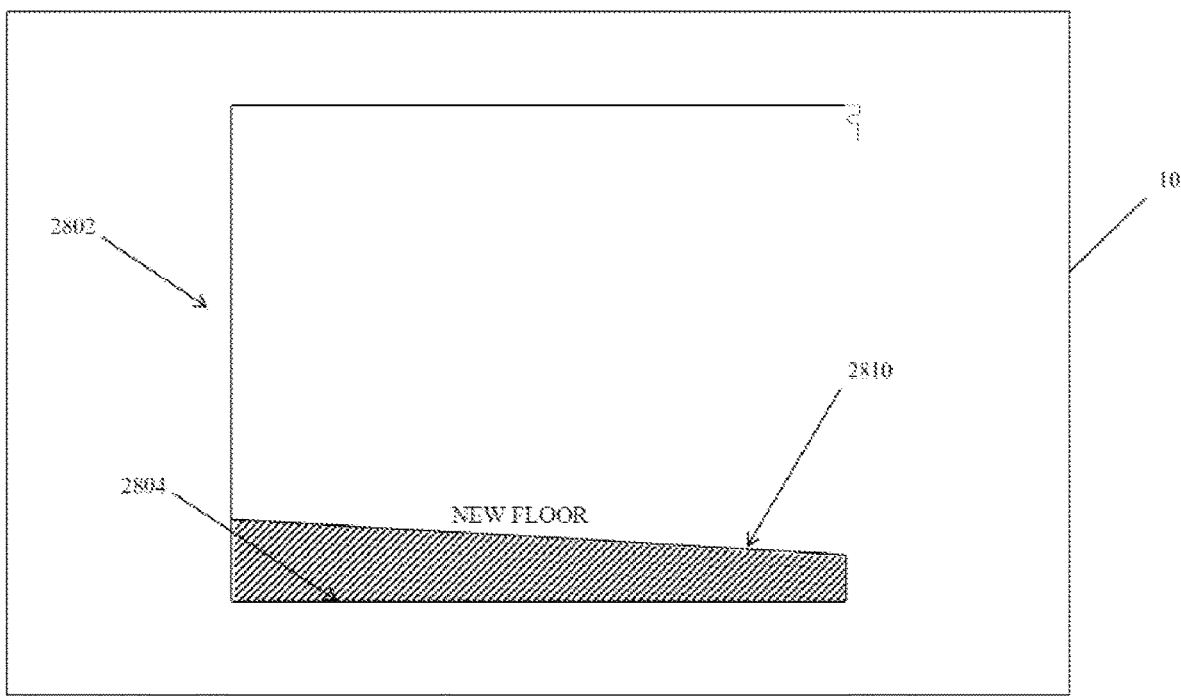
FIG. 31 is an internal view of an exemplary sterilizing cabinet suitable for use in practicing exemplary embodiments of this disclosure.

Shown in FIG. 31 is the interior of sterilizing cabinet 2802 with bottom 2804, and raised floor 2810 within the autoclave 10. As is shown, raised floor 2810 is above bottom 2804 and is angled relative to bottom 2804 such that a flow of condensate is directed toward the vent port of sterilizing cabinet 2802. It should be appreciated that exemplary embodiments of raised floor 2810 can include both substantially planar and curved or featured (with channels) embodiments that direct condensate toward a vent port on sterilizing cabinet 2802, or toward another outlet that allows condensate to drain or exit the interior of sterilizing cabinet 2802.

Figure 32:
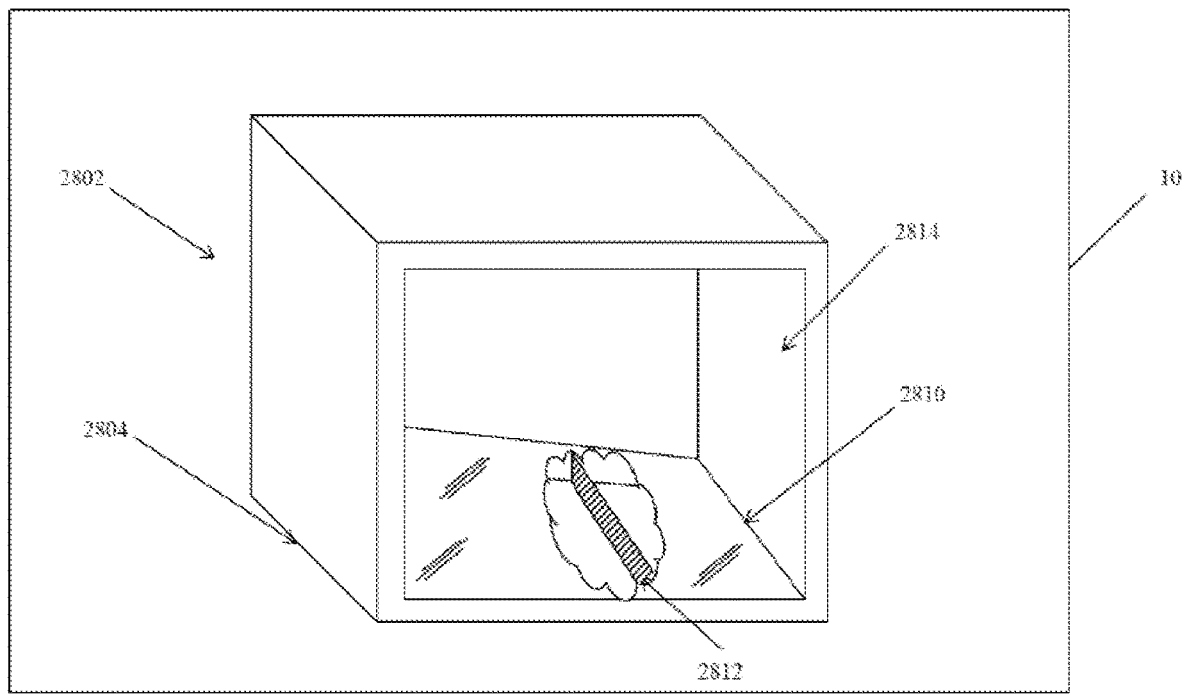
FIG. 32 is an internal view of an exemplary sterilizing cabinet suitable for use in practicing exemplary embodiments of this disclosure.

Shown in FIG. 32 is sterilizing cabinet 2802, bottom 2804, raised floor 2810, raised floor supports 2812, and vent port 2814 within the autoclave 10. Raised floor supports 2812 provide support for the position of raised floor 2810 with sterilizing cabinet 2802. As shown in FIG. 32, raised floor supports 2812 are beams located under raised floor 2810 that are connected to raised floor 2810 and bottom 2804 to maintain the position of raised floor 2810. It should be appreciated that raised floor supports 2812 can include any known beam or support that is able to maintain the position of raised floor 2810 with the weight of the anticipated loaded sterilizing cabinet 2802, which can be up to a 250 pound load or more.

As illustrated in FIG. 32, raised floor 2810 is flush with the bottom of vent port 2814. Exemplary embodiments of raised floor 2810 include instances wherein raised floor 2810 is flush or nearly flush with the bottom of vent port 2814. Exemplary embodiment of raised floor 2810 are positioned relative to the bottom of vent port 2814 such that a flow of condensate along raised bottom 2810 can move and progress through vent port 2814. Raised floor 2810 in the embodiment shown, is tilted or angled relative to bottom 2804 toward vent port 2814 such that any fluid or condensate on raised floor 2810 is moved towards vent port 2814.

In operation, the autoclave receives the sterilizing cabinet and subjects the sterilizing cabinet to a sterilization cycle. As set forth above, the sterilization can include, but is not limited to heat, steam, pressure, gas, plasma, irradiation, chemical components, chemical vapor or combinations thereof.

Thus, the sterilizing cabinet is retained within the autoclave, and the interior environment of the autoclave is controlled to provide a sterilization cycle. The autoclave typically creates a sealed environment which is thus applied to the retained sterilizing cabinet. The autoclave thus subjects the sterilizing cabinet and the interior of the sterilizing cabinet to the sterilization cycle.

The interface between the filters and the sterilizing cabinet is effectively sealed either prior to or during or at the completion of the sterilization cycle. That is, at least before the autoclave is opened, a sealed interface is formed between the seals and the sterilizing cabinet. It is understood the seal between the filter and the sterilizing cabinet may go through a transformation during the sterilization cycle. When the filter is initially operably located relative to the sterilizing cabinet, a seal can be formed. However, it is contemplated that the initial operable location of the seal relative to the sterilizing cabinet may not form a seal, wherein the sealed interface is formed during the sterilization cycle or at the completion of the sterilization cycle.

The seal, when exposed to the sterilization cycle, (in select cases, heat in the form of steam, and pressure) may under goes slight transformation of the seal configuration, and either becomes more form fitting to the sealing surface area or even results in seal formation. This change in the seal during the sterilization cycle may create a more robust seal than when it was originally placed. It is contemplated a variety of materials can be used to enhance or form a seal between the filter (or the cartridge) and the sterilizing cabinet, such as but not limited to card stocks, thermoplastics, thermoplastic elastomers, polymers and waxes.

Thus, the interface between the filters and the sterilizing cabinet can be dynamic, forming a seal during the sterilization cycle, or static, entering the sterilization cycle with the sealed interface and maintaining the sealed interface throughout the sterilization cycle.

Before the autoclave is opened, that is before the sterilized environment of the autoclave is exposed to ambient environment, the interior of the sterilizing cabinet should have no more than a certain amount of moisture and a seal exist between any filter, or cartridge and the sterilizing cabinet. Thus, it is advantageous for a sterilizing cabinet to have only an amount of condensate that can be driven off or evaporated by the autoclave during a normal, or given or predetermined sterilizing cycle of the autoclave or during the post-sterilization cool down period.

In conjunction with any cycle time for removing condensate, the inclined surface in the sterilizing cabinet induces a flow of the condensate to and through a port, such as a filter. The cycle time can be decreased by facilitating the removal of condensate from the sterilizing cabinet during the sterilization cycle. That is, by draining condensate from the sterilizing cabinet during the sterilization cycle, the amount of condensate to be evaporated from within the sterilizing cabinet during the sterilization cycle, or during the post-sterilization cool down period, is decreased, thereby increasing efficiency of the process.

Further exemplary embodiments according to this disclosure include the following embodiments below. Embodiment 1: A sterilizing assembly, comprising: (a) a sterilizing cabinet; (b) a first tray and a second tray sized to be retained within the cabinet; and (c) at least one removable spacer intermediate the first tray and the second tray, the spacer being sterilizable and vertically separating the first tray and the second tray by a given height, the spacer inhibiting lateral displacement of the first tray relative to the second tray, wherein the given height is sufficient to permit a passage of a sufficient quantity of a sterilizing agent between the first tray and the second tray for a predetermined time.

Embodiment 2: The sterilizing assembly according to embodiment 1, wherein the at least one removable spacer is fenestrated.

Embodiment 3: The sterilizing assembly according to embodiment 1, further comprising a second removable spacer, the second removable spacer being sterilizable and located intermediate to one of the first tray and the second tray and the sterilizing cabinet.

Embodiment 4: The sterilizing assembly according to embodiment 1, wherein the given height is at least 0.1 inches.

Embodiment 5: The sterilizing assembly according to embodiment 1, wherein the given height is sufficient to permit passage of a sterilizing agent.

Embodiment 6: The sterilizing assembly according to embodiment 1, wherein the at least one removable spacer includes a shaped wire.

Embodiment 7: The sterilizing assembly according to embodiment 1, wherein the first tray defines an open top and the at least one removable spacer is sized to span the open top.

Embodiment 8: The sterilizing assembly according to embodiment 1, wherein the first tray is free of a lid.

Embodiment 9: The sterilizing assembly according to embodiment 1, wherein the at least one removable spacer and the second removable spacer are sterilizable only once.

Embodiment 10: A method of loading a sterilizing cabinet, the method comprising: (a) loading a sterilizable first pan and a sterilizable second pan within the sterilizing cabinet; and (b) placing a removable and sterilizable spacer between the first pan and the second pan, the spacer (i) providing at least one of a predetermined vertical spacing between the first pan and the second pan and (ii) inhibiting horizontal displacement of the first pan relative to the second pan.

Embodiment 11: The method according to embodiment 10, wherein at least one of the first pan and the second pan is lid free.

Embodiment 12: The method according to embodiment 10, wherein the vertical spacing is sufficient to permit passage of a sterilizing agent.

Embodiment 13: The method according to embodiment 10, wherein the predetermined vertical spacing is at least 0.1 inches.

Embodiment 14: The method according to embodiment 10, further comprising loading a sterilizable third pan and a sterilizable fourth pan within the sterilizing cabinet and placing a second sterilizable spacer to individually vertically space the sterilizable second pan relative to the sterilizable third pan and placing a third sterilizable spacer to individually vertically space the sterilizable third pan relative to the fourth pan independent of the first pan and the second pan.

Embodiment 15: The method according to embodiment 10, wherein the sterilizable spacer between the first pan and the second pan provides a predetermined vertical spacing between the first pan and the second pan.

Embodiment 16: A method of sterilizing, the method comprising: (a) loading a tray retaining a surgical instrument in a sterilization cabinet; (b) sealing a primary filter relative to a vent port in the sterilization cabinet; (c) sealing a secondary filter relative to the vent port and independent of the primary filter; and (d) passing a sterilizing agent through the secondary filter and the primary filter. For the purposes of this disclosure surgical instruments includes implantable materials or devices as well as instruments used for conducting surgeries and medical procedures.

Embodiment 17: The method according to embodiment 16, further comprising removing the secondary filter to retain the sealed primary filter and sterilization cabinet.

Embodiment 18: A sterilizable pan assembly, comprising: (a) a first sterilizable pan having an open top, a closed bottom and a pair of projecting spacer legs; and (b) a second sterilizable pan having an open top and a closed bottom, (c) the spacer legs configured to releasably engage a portion of the second pan and maintain a predetermined vertical spacing between the bottom of the first pan and the top of the second pan.

Embodiment 19: The sterilizable pan assembly according to embodiment 18, wherein the predetermined vertical spacing between the bottom of the first pan and the top of the second pan is at least 0.1 inches.

Embodiment 20: The sterilizable pan assembly according to embodiment 18, wherein the predetermined vertical spacing between the bottom of the first pan and the top of the second pan is sufficient to permit passage of a sterilizing agent.

Embodiment 21: A filtering assembly, comprising: (a) a primary filter holding portion for holding a primary filter for overlying a vent port and forming a sealed interface with a sterilizing cabinet; and (b) a secondary filter holding portion for holding a secondary niter, moveably attached to the primary filter holding portion for overlying the primary filter holding portion and forming a sealed interface with the primary filter holding portion.

Embodiment 22: The filtering assembly according to embodiment 21, wherein the primary filter and the secondary filter are different colors.

Embodiment 23: The filtering assembly according to embodiment 21, wherein the primary filter holding portion and the secondary filter holder portion are hingedly attached.

Embodiment 24: The filtering assembly according to embodiment 21, wherein the secondary filter and the primary filter are coextensive.

Embodiment 25: The filtering assembly according to embodiment 21, wherein the secondary filter and the primary filter have different filter properties.

Embodiment 26: The filtering assembly according to embodiment 21, wherein the secondary filter and the primary filter have similar filter properties.

Embodiment 27: A filter comprising: (a) a center portion of porous material with a predetermined density; and (b) an edge portion of porous material.

Embodiment 28: The filter according to embodiment 27, wherein the edge portion further comprises raised silicone beads.

Embodiment 29: The filter according to embodiment 27, wherein the edge portion is thicker than the center portion.

Embodiment 30: The filter according to embodiment 27, wherein the edge portion comprises at least two layers of folded material.

Embodiment 31: The filter according to embodiment 27, wherein the predetermined density of the center portion allows for passage of a sterilizing agent through the center portion and prevents passage of nongaseous agents.

Embodiment 32: A filter cartridge, the filter cartridge comprising: (a) a frame, the frame comprising a rigid or flexible edge portion and defining a hollow center portion; and (b) a filter, the filter comprising a porous material and being affixed to the frame, the porous material being able to pass only gaseous materials through its surface, wherein the filter cartridge provides sufficient integrity to form a sealed interface with a confronting surface.

Embodiment 33: The filter cartridge according to embodiment 32, the filter cartridge further comprising a second filter, the second filter comprising a porous material and being affixed to the frame, the porous material being able to pass only gaseous materials through its surface.

Embodiment 34: The filter cartridge according to embodiment 32, the filter cartridge further comprising a second frame, the second frame comprising a rigid or flexible edge portion and defining a hollow center portion, the second frame being affixed to the filter.

Embodiment 35: The filter cartridge according to embodiment 34, the filter cartridge further comprising a second filter, the second filter comprising a porous material and being affixed to the second frame and the filter, the porous material being able to pass only gaseous materials through its surface.

Embodiment 36: The filter cartridge according to embodiment 32, wherein the filter is removeably affixed to the frame.

Embodiment 37: The filter cartridge according to embodiment 32, wherein the frame and filter are coextensive.

Embodiment 38: The filter cartridge according to embodiment 32, wherein the frame and the filter are integral.

The present system is distinguished from prior trays which were wrapped with filter media, then disposed in an autoclave and transported to the surgical field after the sterilization process, in that there is no sterilizing container having a plurality of sidewalls and an opening for receiving an instrument tray, with a filter occluding a venting pass through area and the ratio of venting pass through area to volume of the sterilizing container being at least 0.008 inch$^2$ per inch$^3$ (or 1 square inch:125 cubic inches) and in further configurations the ratio being from 0.16 to 6 inch$^2$ per inch$^3$ (or 4 square inches:25 cubic inches to 6 square inches:1 cubic inch).

Further, the sterilization container of the present system can accommodate trays with instruments or devices in the tray, wherein the instruments or devices may or may not be wrapped with filter paper and the tray may or may not be wrapped with filter paper. Thus, it is contemplated the sterilization container can retain unwrapped trays with instruments or devices, wrapped trays with instruments or devices, unwrapped instruments or devices as well as wrapped instruments or devices wherein the ratio of the venting pass through area to volume of the sterilization container provides drying times less than 30 minutes and in select configurations less than 15 minutes after the sterilization cycle.

While select configurations may include a drain for passing condensate from the interior of the sterilization container, it is contemplated that other configurations having the present ratio of venting pass through area to volume can provide the reduced drying time (such as 10 minutes) without draining the condensation. In a further configuration, the floor of the sterilization container can be configured to collect or pool condensation within the container.

What is claimed is:

1. A sterilization container sized to be received in a sterilizer for sterilizing instruments in the sterilizer using a sterilizing agent, the sterilization container comprising:
   (a) an opening defined by a perimeter of an enclosing wall, the enclosing wall defining an interior volume sized to receive a plurality of instrument trays;
   (b) a door moveable between an open position and a closed position, wherein the interior volume is accessible through the opening to permit passage of the plurality of instrument trays when the door is in the open position; and
   (c) a filter cartridge having a gasket surrounding a first filter comprising a porous material wherein the filter cartridge is removably secured to the door when the door is in the open position, wherein the gasket is positioned between the door and the enclosing wall to form a sealed interface between at least one of the door and the enclosing wall when the door is in the closed position, and wherein a sealed periphery between the door and the enclosing wall is broken when the door is opened.

2. The sterilization container of claim 1 further comprising a filter support overlapping at least a portion of the filter cartridge.

3. The sterilization container of claim 2 wherein the filter support is a vented area of the door.

4. The sterilization container of claim 2 wherein the filter support is a set of bars traversing the opening.

5. The sterilization container of claim 3 wherein the door and the enclosing wall define a total surface area, and wherein the first filter and filter support define a venting pass through area, wherein the venting pass through area is at least 5.7% of the total surface area.

6. The sterilization container of claim 1 wherein the filter cartridge further comprises a second filter, the second filter comprising a porous material.

7. The sterilization container of claim 1 wherein the gasket is a compressible seal.

8. The sterilization container of claim 1 wherein the door further comprises tabs or catches located along a perimeter of the door for holding the filter cartridge adjacent the door.

9. The sterilization container of claim 1 wherein the filter cartridge is single-use and disposable.

10. The sterilization container of claim 1 wherein the door includes a fenestrated grid.

11. A sterilization container sized to be received in a sterilizer for sterilizing instruments in the sterilizer using a sterilizing agent, the sterilization container comprising:
   (a) an enclosing wall and a door defining a total surface area and an interior volume sized to receive a plurality of instrument trays, the door defining a venting pass through area, wherein the door is moveable between an open position to permit passage of the plurality of instrument trays and a closed position, and wherein the interior volume is accessible when the door is in the open position; and
   (b) a filter cartridge having a gasket surrounding a first filter, wherein the filter cartridge provides sufficient structural integrity to form a sealing interface with at least one of a confronting surface of the enclosing wall and the door, wherein the first filter occludes the venting pass through area, wherein the venting pass through area is at least 5.7% of the total surface area, and wherein a sealed periphery between the door and the enclosing wall is broken when the door is opened.

12. The sterilization container of claim 11 wherein the filter cartridge forms a sealing interface with both the confronting surface of the enclosing wall and the door.

13. The sterilization container of claim 11 wherein the gasket is affixed to the first filter to be one of a coextensive, permanently affixed, or integral gasket.

14. The sterilization container of claim 11 wherein the filter cartridge is single-use and disposable.

15. The sterilization container of claim 11 wherein the venting pass through area is between approximately 5.7% and 20% of the total surface area.

16. The sterilization container of claim 11 wherein the door comprises tabs or catches located along a perimeter of the door for holding the filter cartridge adjacent the door.

17. The sterilization container of claim 11, wherein the filter cartridge further comprises a second filter, the second filter being affixed to the gasket opposite the first filter.

* * * * *